United States Patent
Sue et al.

(10) Patent No.: US 6,329,492 B1
(45) Date of Patent: Dec. 11, 2001

(54) PHENYL, NAPHTHYL OR FLUORENE CYCLOPENTYL EPOXY RESINS

(75) Inventors: Haruaki Sue, Tsukuba; Shinsuke Hagiwara, Shimodate; Fumio Furusawa, Yuki; Seiichi Akagi, Ibaraki-ken; Akihiro Kobayashi; Hideki Yokoyama, both of Ichihara, all of (JP)

(73) Assignee: Hitachi Chemical Company, Ltd., Tokyo (JP)

( * ) Notice: Subject to any disclaimer, the term of this patent is extended or adjusted under 35 U.S.C. 154(b) by 0 days.

(21) Appl. No.: 09/319,487

(22) PCT Filed: Dec. 1, 1997

(86) PCT No.: PCT/JP97/04373

§ 371 Date: Aug. 13, 1999

§ 102(e) Date: Aug. 13, 1999

(87) PCT Pub. No.: WO98/23568

PCT Pub. Date: Jun. 4, 1998

(30) Foreign Application Priority Data

Nov. 29, 1996 (JP) ..................................................... 8-320118
Feb. 27, 1997 (JP) ..................................................... 9-043512

(51) Int. Cl.[7] .......................... C08G 59/06; C07D 301/28
(52) U.S. Cl. ........................... 528/97; 525/396; 525/523; 528/98; 549/522
(58) Field of Search ............................ 549/522; 525/396, 525/523; 528/97, 98

(56) References Cited

U.S. PATENT DOCUMENTS

| 3,332,908 | 7/1967 | Sellers et al. |
| 3,689,573 | 9/1972 | Klein et al. |
| 3,970,694 | 7/1976 | Minai et al. |

FOREIGN PATENT DOCUMENTS

| 47-014094 Kokai 48-072159 | 4/1972 | (JP) |
| 50-024256 Kokai | 9/1973 | (JP) |
| 60-135427 Kokai | 3/1975 | (JP) |
| | 7/1985 | (JP) |

OTHER PUBLICATIONS

Hassan et al., Chemical abstracts accession No. 1974:553182, Indian Journal of Technology (1974), vol. 12, No. 3, pp. 120–122.*

S. Kanemasa et al., "di–Selective Reductive Coupling/Dieckmann Condensation Sequence of alpha–, beta–Unsaturated Amides with Samarium (II) Iodide/HMPA", Tetrahedron Letters, vol. 37, No. 47, Nov. 18, 1996, pp. 8505–8506.

D. Rao et al., "Indirect Hydroxylation of Phenols", Tetrahedron Letters, vol. 22, No. 25, 1981, pp. 2337–2340.

P. Bartlett et al., "Rearrangement of 10–oxabenzo–syn–sesquinorbornene", Tetrahedron Letters, vol. 26, No. 22, 1985, pp. 2615–2616.

* cited by examiner

Primary Examiner—Robert E. L. Sellers
(74) Attorney, Agent, or Firm—Griffin & Szipl, P.C.

(57) ABSTRACT

This invention provides a compound suitable as an encapsulating material for electronic devices and having a high Tg, low moisture-absorptive, high adhesion and rich fluidity, which is a cyclopentylene compound represented by Formula (I) and its intermediate cyclopentenyl compound represented by Formula (III). In the formula, m is 0 or more, $Ar^1$ and $Ar^2$ are each a phenol residual group, a naphthol residual group or a fluorene derivative residual group, and each contain a hydroxyl group or a glycidyloxyl group.

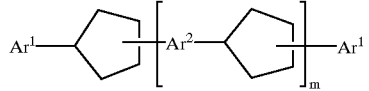

(I)

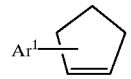

(III)

15 Claims, 16 Drawing Sheets

PHENYL, NAPHTHYL OR FLUORENE CYCLOPENTYL EPOXY RESINS

TECHNICAL FIELD

This invention relates to a cyclopentylene compound useful as a material for encapsulating electronic devices, for lamination or for adhesion, an epoxy resin composition and a molding material for encapsulating electronic devices which composition and material contain the compound, and a resin-encapsulated electronic device encapsulated with the composition.

BACKGROUND ART

Molding materials containing epoxy resin are commonly put into wide use for the encapsulating of electronic devices such as transistors and ICs (integrated circuits). This is because the epoxy resin is well balanced in various properties such as electrical properties, moisture resistance, thermal resistance, mechanical properties and adhesion to inserts. In particular, a combination of o-cresol novolak epoxy resin with phenol novolak curing agent is very well balanced in these properties, and hence widely used as a base resin for IC-encapsulating molding materials.

In recent years, as electronic devices have come to be packaged in a high density, conventional packages of a pin-insertion type have shifted to packages of a surface-mounting type, and the latter is prevailing. In surface-mounting ICs, packages show a tendency to be made thin and compact so that packaging density can be made higher and packaging height can be made smaller. Accordingly, encapsulating mediums have come to be applied in a very small thickness because the volume held by device elements in a package must be made relatively larger.

Such surface-mounting packages differ from the conventional pin-insertion packages in the manner of packaging. In a packaging step for the pin-insertion packages, pins are inserted to a wiring board and thereafter these are soldered on the back of the wiring board. Hence, device elements are by no means directly exposed to high temperature. On the other hand, in a packaging step for the surface-mounting package, devices are provisionally fastened to the surface of a wiring board and then soldered by means of a solder bath or a reflowing assembly. Hence, the device elements are exposed to high temperature. As the result, in instances where a package has moistened, the absorbed moisture may expand abruptly at the time of soldering to crack the package. At present, this phenomenon is a serious problem in the fabrication of surface-mounting ICs.

In IC packages encapsulated with a usual base resin composition, the above problem is unavoidable. Hence, measures are taken such that ICs are moistureproof-wrapped to send them, or ICs are beforehand well dried to use them and then mounted on a wiring board. These measures, however, take much time and also require a high cost.

Accordingly, IC-encapsulating molding materials making use of a biphenyl skeleton type epoxy resin having a good moisture absorption and moisture resistance have been put into practical use for thin-type packages, because of its superior reflow crack resistance. This biphenyl skeleton type epoxy resin, however, has a problem that it has a low Tg (glass transition temperature), and there are limits within which this resin is usable.

DISCLOSURE OF THE INVENTION

The present invention was made taking account of the above problem. A first object of the present invention is to provide a novel compound and an intermediate thereof which are suited as an encapsulating material for electronic devices, having high general-purpose properties, being low moisture-absorptive, having a high adhesion and being rich in fluidity.

A second object of the present invention is to provide a molding material which enables to solder without taking any measure against moisture absorption, e.g., any special pretreatment or wrapping, and a resin-encapsulated electronic device whose elements have been encapsulated with the molding material.

The present inventors have discovered that a cyclopentenylphenol compound obtained by allowing cyclopentadiene to react with a naphthol compound, a phenol compound and/or a fluorene compound in the presence of a specific acid under specific reaction conditions is effective for solving the above problem, and, on the basis of this discovery, they have accomplished the present invention.

To achieve the first object, the present invention provides a first cyclopentylene compound represented by the following general formula (I) (hereinafter "compound I") and a second cyclopentylene compound represented by the following general formula (II) (hereinafter "compound II").

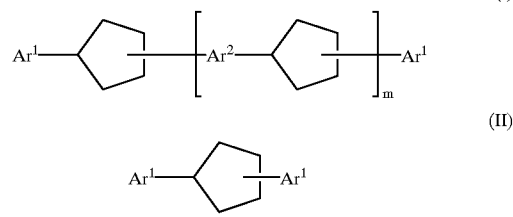

In these formulae, m represents a positive number.
$Ar^1$ represents at least one of monovalent organic groups represented respectively by

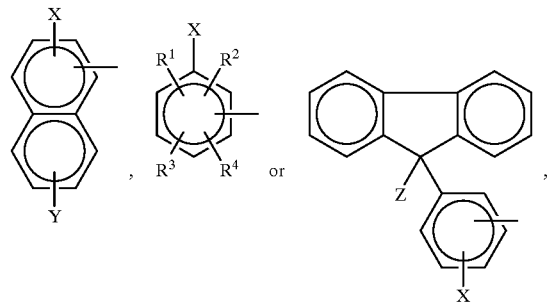

$Ar^2$ represents at least one of divalent organic groups selected from a first atomic group represented by

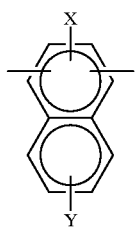

a second atomic group represented by

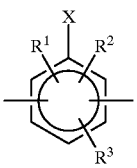

and a third atomic group represented by

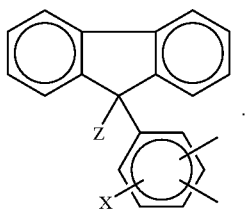

In the foregoing, X represents a hydroxyl group, or a 2,3-epoxypropoxyl group (i.e., a glycidyloxyl group)

Y represents a hydrogen atom, a hydroxyl group or a 2,3-epoxypropoxyl group. Here, $R^1$ to $R^4$ are each a group selected independently from a hydrogen atom, an alkyl group and an aryl group having 1 to 10 carbon atoms, and a halogen atom, and at least one of them may preferably be a hydrogen atom. Z represents a hydrogen atom, a phenyl group, a hydroxyphenyl group or a 2,3-epoxypropoxyphenyl group. In view of readiness for production, Z may preferably be a 4-hydroxyphenyl group or a 4-(2,3-epoxypropoxy) phenyl group.

There are no particular limitations on the position at which the cyclopentylene group is bonded to the naphthalene ring and the benzene ring. For example, in the case of fluorenes, the cyclopentylene group may be bonded to the 3- or 5-position, the 2-position or the 3-position when the hydroxyl group is bonded at the 2-position, the 3-position or the 4-position of the benzene ring, respectively. Such fluorenes can be relatively readily synthesized and are preferred.

The number m of repeating units may preferably be not more than 20 on the average, and particularly preferably not more than 10 on the average, in order to materialize in the compound I the above prescribed properties in a well balanced state. Also, the groups $Ar^2$ in one molecule may all be like atomic groups, or two or more of the first to third atomic groups may be contained in one molecule.

In the case of a compound containing two or more atomic groups (i.e., a cooligomer), its form of polymerization may be any of a random copolymer, an alternating copolymer, a block copolymer and a graft copolymer. In the case of a cooligomer containing the both first and second atomic groups, the number of first atomic groups and the number of second atomic groups in one molecule may preferably be in a ratio of from 20:1 to 1:20, and particularly preferably from 10:1 to 1:10.

In particular, in the molding material for encapsulating electronic devices, when the cyclopentylene compound of the present invention having a phenolic hydroxyl group is used as an epoxy resin curing agent, the above polymerization ratio (number of first atomic groups number of second atomic groups) may particularly preferably be 2:1 to 1:9, and, when the cyclopentylene compound of the present invention in which X is a 2,3-epoxypropoxyl group is used as an epoxy resin, the ratio may particularly preferably be 4:1 to 1:4.

A compound containing as the groups $Ar^2$ the third atomic group in addition to the first atomic group and/or the second atomic group is particularly preferred because of its superior thermal resistance. This third atomic group may preferably be in a content of from 10 to 20 mol % of the total number of groups $Ar^2$ in the molecule.

The present invention also provides as an intermediate for producing the above cyclopentylene compound a cyclopentenyl compound represented by the following general formula (III).

(III)

wherein $Ar^1$ represents any one of monovalent organic groups represented respectively by

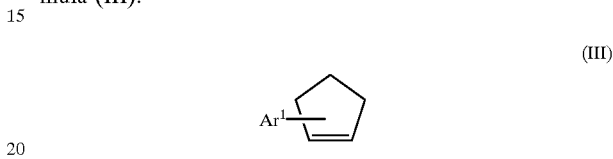

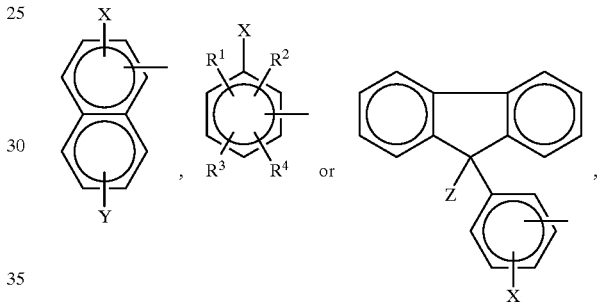

X, Y, Z and $R^1$ to $R^4$ are the same as defined in the case of Formulae (I) and (II).

In the above general formula (III), the cyclopentenyl group may preferably be a 2-cyclopenten-1-yl group in view of the reactivity in synthesizing the cyclopentylene compound, and may also be a 3-cyclopenten-1-yl group.

The cyclopentylene compound of the present invention may be used as a component of the epoxy resin composition as an epoxy resin curing agent when it contains a phenolic hydroxyl group and as an epoxy resin when it contains a 2,3-epoxypropoxyl group. Accordingly, in order to achieve the above second object, the present invention provides;

(1) an epoxy resin composition comprising a modified phenol resin which is a first and/or second cyclopentylene compound wherein at least one of X, Y and Z is a phenolic hydroxyl group (hereinafter "compound Ia, IIa", respectively), and an epoxy resin having two or more epoxy groups in one molecule; and (2) an epoxy resin composition comprising an epoxy resin which is a first and/or second cyclopentylene compound wherein at least one of X, Y and Z is a 2,3-epoxypropoxyphenyl group (hereinafter "compound Ib, IIb", respectively), and an epoxy resin curing agent.

The epoxy resin composition of the present invention has superior low moisture absorption, superior fluidity at the time of molding and superior thermal resistance together, and hence can be used in a wide range of fields as a material for encapsulating electronic devices, and also as an anisotropic conductive film material, an insulating material, a laminated sheet material, an adhesive and so forth.

The cyclopentylene compound and epoxy resin composition of the present invention are especially suited for use in materials for encapsulating electronic devices. Accordingly, the present invention provides an epoxy resin molding material for encapsulating electronic devices which contains the first and/or second cyclopentylene compound(s) (compound I, II), and also provides a resin-encapsulated electronic device comprising a device element encapsulated with an encapsulating member containing a cured product of the molding material.

BEST MODES FOR PRACTICING THE INVENTION

A. Synthesis of Cyclopentenyl Addition Product

Figure 1:
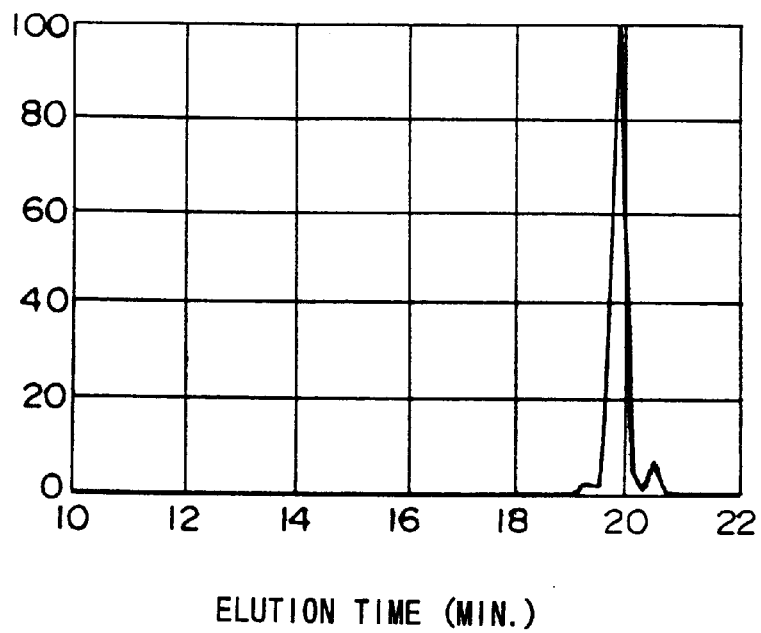
FIG. 1 shows a GPC chromatogram of 2,6-dimethyl-4-(2-cyclopenten-1-yl)phenol.

Of the cyclopentenyl addition products represented by general formula (III) (hereinafter "compound III") of the present invention, the compounds in which X is a hydroxyl group (hereinafter "compound IIIa") can be synthesized by allowing a naphthol compound, a phenol compound or a fluorene compound to react with cyclopentadiene in the presence of an acid catalyst, as shown by the following reaction scheme. Any of these naphthol, phenol and fluorene may be used alone or in combination of two or more.

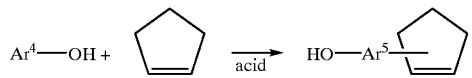

(Compound IIIa)

wherein Ar$^4$—OH is

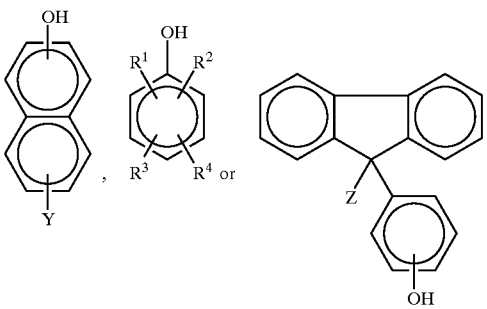

and Ar$^5$—OH is

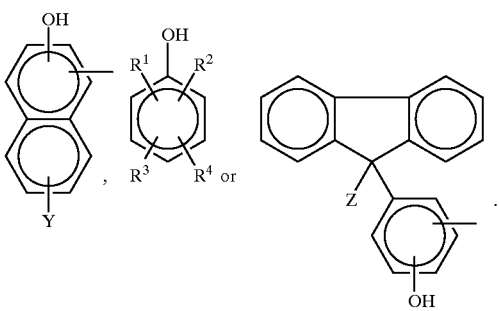

Here, Y, Z and R$^1$ to R$^4$ are the same as defined in the case of general formula (I).

The naphthol compound

usable in this reaction may include 1-naphthol, 2-naphthol, 1,5-dihydroxynaphthalene, 1,6-dihydroxynaphthalene, 1,7-dihydroxynaphthalene or 2,7-dihydroxynaphthalene. Any of these may be used alone or in combination of two or more.

The phenol compound

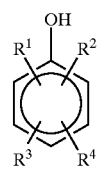

may include phenol, o-cresol, p-cresol, m-cresol, butylphenol, xylenol, nonylphenol or fluorenes. Phenol compounds used in synthesis for usual phenol resins may be used. Any of these may be used alone or in combination of two or more.

The fluorene compound

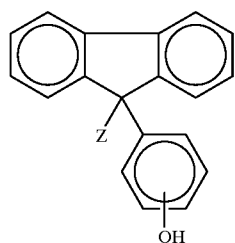

may include 9,9-bis(hydroxyphenyl)fluorene, 9-(hydroxyphenyl)fluorene or 9-(hydroxyphenyl)-9-phenylfluorene. The substitution position of the hydroxyl group may be any of the 2-, 3- and 4-positions of the phenyl group. In view of readiness for production, the 4-position is preferred. Any of these may be used alone or in combination of two or more.

As the acid catalyst, various acids may be used, including strong acids such as hydrochloric acid, sulfuric acid, p-toluenesulfonic acid, trifluoroacetic acid and phosphoric acid; Lewis acids such as boron trifluoride, aluminum chloride and molybdenum chloride; and superstrong acids (those in which Hammett's acidity function $H_0$ is a negative value having a larger absolute value than that of 100% sulfuric acid ($H_0$=−11.93) such as trifluoromethanesulfonic acid, pentafluoroethanesulfonic acid, chlorosulfonic acid and methylsulfonic acid. Any of these acid catalysts may be used alone or in combination of two or more.

The acid catalyst may be used in an amount of from 0.05 mole to 1 mole, and preferably from 0.1 mole to 0.5 mole, per mole of the total amount of the naphthol compound, phenol compound and fluorene compound. So long as the catalyst is in the amount of at least 0.05 moles per mole of the total amount of the naphthol compound, phenol compound and fluorene compound, a reaction rate which is industrially of no problem can be attained, desirably. Also, so long as it is in an amount not more than 1 moles, the catalyst can be removed from the product with ease, desirably.

The molar ratio of the naphthol compound, phenol compound and/or fluorene compound to the cyclopentadiene may be in the range of from (naphthol compound, phenol compound and/or fluorene compound)/cyclopentadiene=3/1 to 1/2, and more preferably in the range of from 2/1 to 1/1.5. So long as this molar ratio is 3/1 or less, the residue of any unreacted naphthol compound, phenol compound and/or fluorene compound can be made less, desirably. Also, so long as it is 1/2 or more, double- or more substituted products can be less formed, desirably.

This cyclopentenyl addition reaction may be carried out in a solvent-free system. In an instance where the naphthol compound, phenol compound or fluorene compound used has a high melting point, an organic solvent may be used so as to improve the yield of the cyclopentenyl addition product. The solvent usable in such an instance may include aromatic organic solvents such as toluene, alcohols such as methanol and ethanol, ethers such as tetrahydrofuran, dioxane and ethyl ether, ketones such as acetone, methyl ethyl ketone and methyl isobutyl ketone, and chlorine-containing organic solvents such as chloroform and chlorobenzene.

This cyclopentenyl addition reaction may be carried out by introducing the naphthol compound, phenol compound and/or fluorene compound, the solvent and the acid catalyst into a reaction vessel and adding the cyclopentadiene (or a solution thereof) dropwise while stirring them, or may be carried out by dissolving the naphthol compound, phenol compound and/or fluorene compound and the cyclopentadiene as they are or in the organic solvent and adding the acid catalyst while stirring the solution.

Reaction temperature may preferably be set in the range of from −30° C. to 150° C. A too low reaction temperature may make the reaction time longer, and a too high reaction temperature may cause dimerization reaction of the cyclopentadiene and polymerization reaction of the cyclopentenyl addition product.

Any unreacted naphthol compound or phenol compound may be removed by a process such as distillation, steam distillation, molecular distillation or extraction.

B. Synthesis of Cyclopentylene Compound

Of the first and second cyclopentylene compounds of the present invention, the compounds wherein X is a hydroxyl group (the compounds Ia, IIa) can be obtained by allowing the above compound IIIa to react with a naphthol compound, a phenol compound and/or a fluorene compound in the presence of an acid catalyst, as shown by the following reaction scheme.

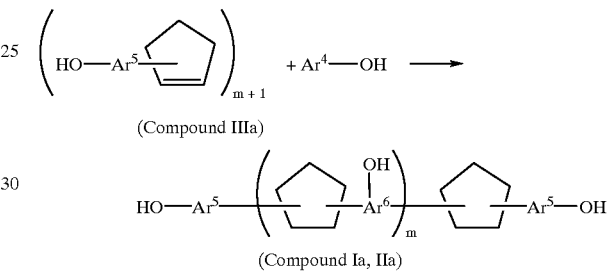

(Compound IIIa)

(Compound Ia, IIa)

wherein $Ar^6$—OH is

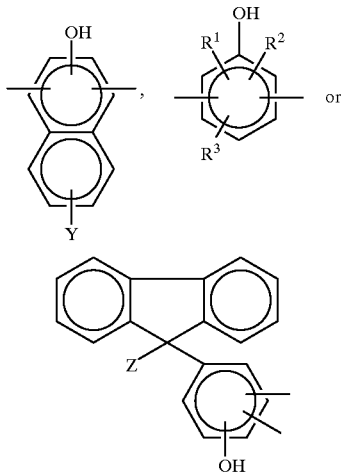

Here, Y, Z and $R^1$ to $R^3$ are the same as defined in the case of general formula (I). Average number m of repeating units is a positive number of 0 or more (preferably 0 to 20).

As the naphthol compound, phenol compound and/or fluorene compound and the acid catalyst, those which are the same as those in the case of the synthesis of the cyclopentenyl addition product described above may be used. Either of those which are the same as and those which are different from those used in the synthesis of the cyclopentenyl addition product may be used. The amount of the acid catalyst used, the reaction solvent and the reaction conditions may also be set alike as in the case of the synthesis of the cyclopentenyl addition product described above.

The number of total equivalent of the naphthol compound, phenol compound and fluorene compound with respect to the cyclopentenyl addition product may appropriately be changed to obtain either of the compound Ia and the compound IIa.

C. Synthesis of Epoxy Compound

The phenolic hydroxyl group of the compound Ia, IIa or IIIa may be converted to synthesize the compound represented by general formula (I), (II) or (III) having the 2,3-epoxypropoxyl group (herein "compound Ib, IIb, IIIb", respectively).

The phenolic hydroxyl group can be converted to the 2,3-epoxypropoxyl group by allowing the compound Ia, IIa or IIIa to react with an epihalohydrin compound in the presence of a basic compound.

As examples of the epihalohydrin compound usable here, it may include epichlorohydrin, epibromohydrin and epiiodohydrin and the like. A mixture of any of these may also be used. Of these, from an industrial viewpoint, it is preferable to use epichlorohydrin.

This reaction of 2,3-epoxypropoxidation (i.e., glycidyl etherification) may be carried out by a known process. For example, the compound Ib, IIb or IIIb can be obtained by a process in which a basic compound (e.g., sodium hydroxide or potassium hydroxide) is added to a mixture of the compound Ia, the epihalohydrin compound (in an amount of 2- to 15-fold moles per mole of the phenolic hydroxyl group of the compound Ia) and a solvent (e.g., dioxane or dimethyl sulfoxide), and the reaction is carried out while keeping the system at 50 to 150° C.

These compounds can also be produced by adding the a quaternary ammonium salt (e.g., tetramethylammonium chloride or tetraethylammonium chloride, in an amount of 0.001- to 0.1-fold mole per mole of the phenolic hydroxyl group of the compound Ia) to the compound Ia to carry out the reaction at a temperature of from 50 to 150° C., and adding to the resultant halohydrin ether a solid or concentrated aqueous solution of sodium hydroxide, potassium hydroxide or the like to further carry out the reaction at temperature of from 50 to 150° C. to effect ring closure.

After the reaction is completed, any unreacted epihalohydrin, organic solvent optionally used and the like may be removed by distillation, and the inorganic salt formed may be separated and removed by a means such as extraction with water or filtration, thus the desired epoxy compound Ib, IIb or IIIb can be obtained.

D. Epoxy Resin Composition and Molding Material for Encapsulating Electronic Devices The epoxy resin composition and molding material for encapsulating electronic devices according to the present invention contain the following cyclopentylene compound (1), and may further appropriately contain components (2) to (5) as occasion calls. The respective components will be specifically described below.

The composition and molding material of the present invention may be prepared by any methods so long as various raw materials therefor can be dispersed and mixed uniformly. A common preparation method may include a method in which raw materials to be compounded in prescribed quantities are thoroughly mixed using a mixer or the like, and thereafter the mixture obtained is melt-kneaded using a mixing roll, an extruder or the like, followed by cooling and pulverization.

(1) Cyclopentylene Compound

The epoxy resin composition and molding material for encapsulating electronic devices according to the present invention contains at least one of the modified phenol resin(s) phenolic-hydroxyl-group-containing compound Ia and/or compound IIa and the epoxy resin(s) glycidyl ether compound Ib and/or compound IIb.

The compound Ia or compound IIa of the present invention may be used as an epoxy resin curing agent. The epoxy resin for which this epoxy resin curing agent of the present invention used is not particularly limited. These compounds can be used as curing agents for any epoxy resins commonly used.

The epoxy resin epoxy-group-containing compound Ib or compound IIb may be allowed to react with an acid anhydride, an amine or a phenolic hydroxyl group to obtain a cured product. Accordingly, the epoxy resin composition and molding material for encapsulating electronic devices which contain the compound Ib or compound IIb of the present invention may preferably further contain an epoxy resin curing agent which is a compound containing such a functional group. Any epoxy resin curing agents commonly used may be used in the present invention.

(2) Epoxy Resin

The epoxy resin usable in the epoxy resin composition and molding material for encapsulating electronic devices according to the present invention includes, e.g., those obtained by epoxidation of novolak resins formed of phenols and aldehydes, including phenol novolak epoxy resin, ortho-cresol novolak epoxy resin and naphthol-cresol novolak epoxy resin; glycidyl ether of bisphenol A, bisphenol F, bisphenol S or alkyl-substituted biphenols; glycidylamine type epoxy resins obtained by reacting polyamines such as diaminodiphenylmethane and isocyanuric acid with epichlorohydrin; linear aliphatic epoxy resins obtained by oxidizing olefin linkages with peracids such as peracetic acid; 4,4'-diglycidyl-3,3'-5,5'-tetramethylbiphenylmethane, having a biphenyl skeleton; and alicyclic epoxy resins.

Especially when an alkyl-substituted biphenol diepoxy resin such as 4,4'-bis(2,3-epoxypropoxy)-3,3', 5,5'-tetramethylbiphenyl is used, the product has good adhesion and moisture absorption, thus a molding material having superior reflow crack resistance and moisture resistance can be obtained. Such an epoxy resin may include those obtained by epoxidation of 4,4'-dihydroxy-3,3', 5,5'-tetramethylbiphenyl with epichlorohydrin. This alkyl-substituted biphenol diepoxy resin may preferably be used in an amount of at least 60% by weight based on the total weight of the epoxy resin, in order for the epoxy resin to exhibit the features such as low moisture absorptivity and high adhesion sufficiently and to be improved in soldering resistance.

These epoxy resins may be used in appropriate combination of any number of kinds. In the case when the compound Ib or IIb of the present invention is contained, any of these epoxy resins may further be used in combination, or may not be used.

(3) Epoxy Resin Curing Agent

Epoxy resin curing agents usable in the epoxy resin composition and molding material for encapsulating electronic devices according to the present invention may include, e.g., compounds having a phenolic hydroxyl group. Such compounds include phenol novolak resin, naphthol novolak resin, orthocresol novolak resin, alicyclic phenol resin, poly(p-vinylphenol) resin, and phenol-aralkyl resin having a xylylene group.

The phenol novolak resin, naphthol novolak resin and orthocresol novolak resin can be obtained by condensation or co-condensation of a phenol compound such as phenol, cresol, xylenol, resorcinol, catechol, bisphenol A or bisphenol F or a naphthol compound such as 1-naphthol, 2-naphthol or dihydroxynaphtalene with an aldehyde compound such as formaldehyde, acetaldehyde, propionaldehyde, benzaldehyde or salicylaldehyde in the presence of an acid catalyst. The phenol-aralkyl resin having a xylylene group can be synthesized from a phenol compound and dimethoxy-p-xylene.

These epoxy resin curing agents may be used in appropriate combination of any number of kinds. In the case when the compound Ia or IIa of the present invention is contained, any of these epoxy resin curing agents may further be used in combination, or may not be used.

In the case when such a curing agent is used, it may preferably be used in such a range that it is not more than the amount of the compound Ia and compound IIa so that the properties of these can be well exhibited.

There are no particular limitations on the amount of the epoxy resin curing agent (inclusive of the modified phenol resin of the present invention). Usually, in order to make unreacted residues of both the resin and the curing agent less occur, it may preferably be added in an equivalent of from 0.5 to 2.5 based on the number of epoxy groups of the epoxy resin. In particular, it may preferably be in an equivalent of from 0.7 to 1.3, when the product is used as the epoxy resin molding material for encapsulating electronic devices or the material for lamination. When used for other purposes (e.g., adhesives and insulating varnishes), it may appropriately be adjusted according to the purposes.

(4) Curing Accelerator

The epoxy resin composition and molding material for encapsulating electronic devices according to the present invention may optionally be incorporated with a curing accelerator in order to accelerate the curing reaction of epoxy resin's epoxy groups with curing agent's phenolic hydroxyl groups.

Such a curing accelerator may include, e.g., diazabicycloalkenes such as 1,8-diazabicyclo(5,4,0)undecene-7, and derivatives thereof; tertiary amines such as triethylenediamine, benzyldimethylamine, triethanolamine, diethylaminomethanol and tris(dimethylaminomethyl) phenol; imidazoles such as 2-methylimidazole, 2-phenylimidazole, 2-phenyl-4-methylimidazole and 2-heptadecylimidazole; organic phosphines such as tributylphosphine, methyldiphenylphosphine, triphenylphosphine, diphenylphosphine and phenylphosphine; tetra-substituted phosphonium tetra-substituted borates such as tetraphenylphosphonium tetraphenylborate, tetraphenylphosphonium ethyltriphenylborate and tetrabutylphosphonium tetrabutylborate; and tetraphenylborates such as 2-ethyl-4-methylimidazole tetramethylborate, 2-ethyl-4-methylimidazole tetraphenylborate and N-methylmorpholine tetraphenylborate; any of which may be used under appropriate selection from among these. In the case when such a curing accelerator is used, it may usually be used in an amount of 0.005 to 3 parts by weight based on the total weight of the epoxy resin composition or molding material for encapsulating electronic devices which is regarded as 100 parts by weight.

(5) Inorganic Filler

The epoxy resin composition and molding material for encapsulating electronic devices according to the present invention may optionally be incorporated with an inorganic filler in order to lower their moisture absorption and coefficient of linear expansion and to improve thermal conductivity and strength. Especially when used as the molding material for encapsulating electronic devices, it is preferable for the molding material to contain the inorganic filler.

The inorganic filler usable in the present invention may include fused silica, crystal silica, alumina, zircon, calcium silicate, calcium carbonate, silicon nitride, boron nitride, beryllia, zirconia and potassium titanate. From the viewpoint of lowering the coefficient of linear expansion, fused silica is preferred among these inorganic fillers. From the viewpoint of high thermal conductivity, alumina is preferred. Also usable are inorganic fillers having a flame-retardant effect, such as aluminum hydroxide, magnesium hydroxide and zinc borate.

These are usually used in the form of powder or sphered beads. These may also be compounded in the form of fibers such as single-crystal fibers and glass fibers. Any of these inorganic fillers may be used alone or in combination of two or more.

In the case when the inorganic filler is incorporated, it may usually be compounded in an amount of from 70 to 93% by weight of the whole epoxy resin composition or molding material for encapsulating electronic devices. From the view point of lowering the coefficient of thermal expansion and improving high-temperature strength, it may preferably be compounded in an amount of 80% by weight or more.

(6) Other Additives

Release agents such as higher fatty acids, higher fatty acid metal salts, ester waxes and polyolefin waxes; colorants such as carbon black; and coupling agents such as epoxysilane, aminosilane, ureidosilane, vinylsilane, alkylsilanes, organic titanates, aluminum alcoholate, methoxysilane and dimethoxysilane may optionally be compounded as other additives.

E. Resin-encapsulated Electronic Device

The resin-encapsulated electronic device of the present invention can be produced by mounting a device element on a support member and encapsulating it with the molding material of the present invention at its necessary portions. As a method for encapsulating electronic devices, low-pressure transfer molding is most commonly used. Injection molding or compression molding may also be used.

The support member usable in the present invention includes lead frames, wired tape carriers, wiring boards, glass, and silicon wafers. The device element includes active elements such as semiconductor chips, transistors, diodes and thyristors, passive elements such as capacitors, resistors and coils, and the like, any of which may appropriately be used according to purposes. The resin-encapsulated electronic device of the present invention may also be one serving as a component part of different devices, or may be one used independently.

The present invention is especially suited for resin-encapsulated semiconductor devices. The electronic device of the present invention may include TCPs (tape carrier packages) obtained by encapsulating a semiconductor chip connected to a tape carrier through bumps, with the molding material of the present invention; and COB (chip-on-board) modules, hybrid ICs and multi-tip modules, obtained by encapsulating a device element with the molding material of the present invention, the device element being connected to wirings formed on a wiring board or glass by wire bonding, flip-chip bonding or soldering.

EXAMPLES

Synthesis examples and working examples of the present invention will be detailed below with reference to the drawings. The present invention is by no means limited to these. In the following synthesis examples and working examples, test methods used are as follows:

Molecular weight distribution and molecular weight:

Measured with a high-speed liquid chromatograph L6000, RI detector, manufactured by Hitachi, Ltd., and a data analyzer C-R4A, manufactured by Shimadzu Corporation. As GPC (gel permeation chromatography) columns used for analysis are G2000HXL and G3000HXL, available from Toso Corporation. Sample concentration is set being 0.2%, tetrahydrofuran is used as the mobile phase and the flow rate is set at 1.0 ml/min to make measurement. Number-average molecular weight is calculated using a calibration curve prepared using a polystyrene reference sample. Number-average molecular weights shown in the following synthesis examples and working examples are all values in terms of polystyrene.

NMR (nuclear magnetic resonance) spectrum:

An FT-NMR spectrometer AC-250, manufactured by Bruker Co., is used, and deuterated chloroform or deuterated methanol is used as a measuring solvent.

FD-MS (field desorption mass spectrometry):

Measured with a Model M-2000 double-focusing mass spectrometer provided with an FD-MS unit, manufactured by Hitachi, Ltd. A sample is dissolved in acetone, and the resultant solution is coated on a carbon emitter to make measurement at an accelerating voltage of 4.0 kV.

Synthesis Example 1

(1) Synthesis of 2,6-Dimethyl-4-(2-cyclopenten-1-yl)phenol

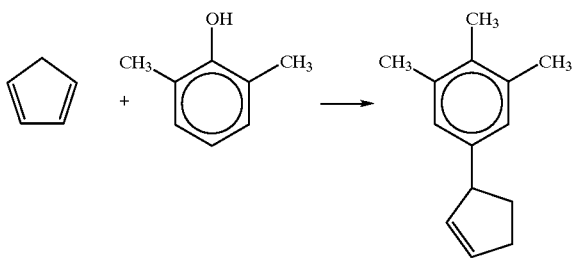

Into a 2-liter flask having a stirrer, a condenser and a thermometer, 366 g of 2,6-dimethylphenol, 360 g of toluene and 102 g of phosphoric acid were introduced, and a solution of mixture of 247 g of cyclopentadiene and 200 g of toluene was added dropwise over a period of 3 hours while stirring the mixture under ice cooling, followed by further stirring for 4 hours at room temperature. To the reaction solution thus obtained, tetrahydrofuran (hereinafter "THF") and methyl isobutyl ketone (hereinafter "MIBK") were added, and the resultant solution was washed with water until it turned neutral, followed by distillation under reduced pressure. After the reaction solvent had evaporated, unreacted 2,6-dimethylphenol evaporated. A fraction at 3 mmHg and 140° C. was 2,6-dimethyl-4-(2-cyclopenten-1-yl)phenol. The results of analysis by GPC thereof are shown in FIG. 1. Its yield determined by GPC was 94% (area ratio).

(2) Synthesis of 1,3-Bis(4-hydroxy-3,5-dimethylphenyl)cyclopentane (Compound IV)

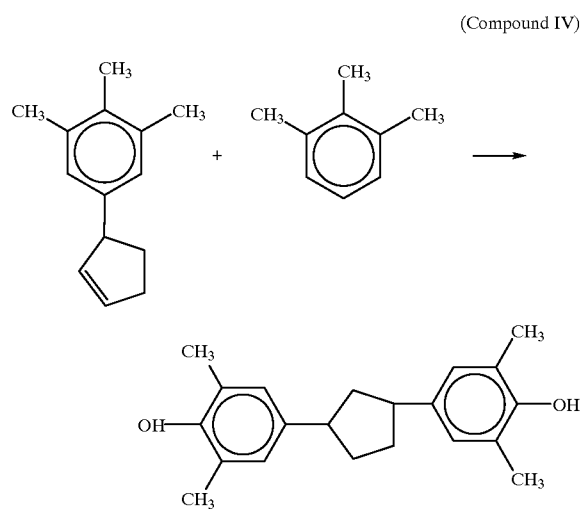

Into a 2-liter flask having a stirrer, a condenser and a thermometer, 286 g of 2,6-dimethylphenol and 40 g of p-toluenesulfonic acid (hereinafter "PTS") were introduced, and a solution of mixture of 106 g of 2,6-dimethyl-4-(2-cyclopenten-1-yl)phenol and 106 g of toluene was added dropwise over a period of 1 hour while stirring the mixture kept at 100° C., followed by further stirring for 4 hours at 80° C. To the reaction solution thus obtained, THF and MIBK were added, and the resultant solution was washed with water until it turned neutral, followed by removal of the solvent and 2,6-dimethylphenol using an evaporator.

Figure 2:
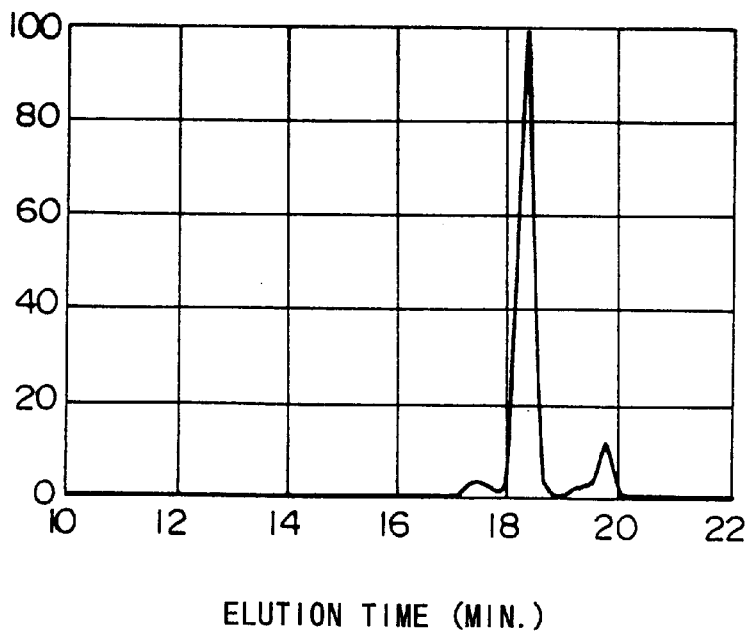
FIG. 2 shows a GPC chromatogram of compound IV.
Figure 3:
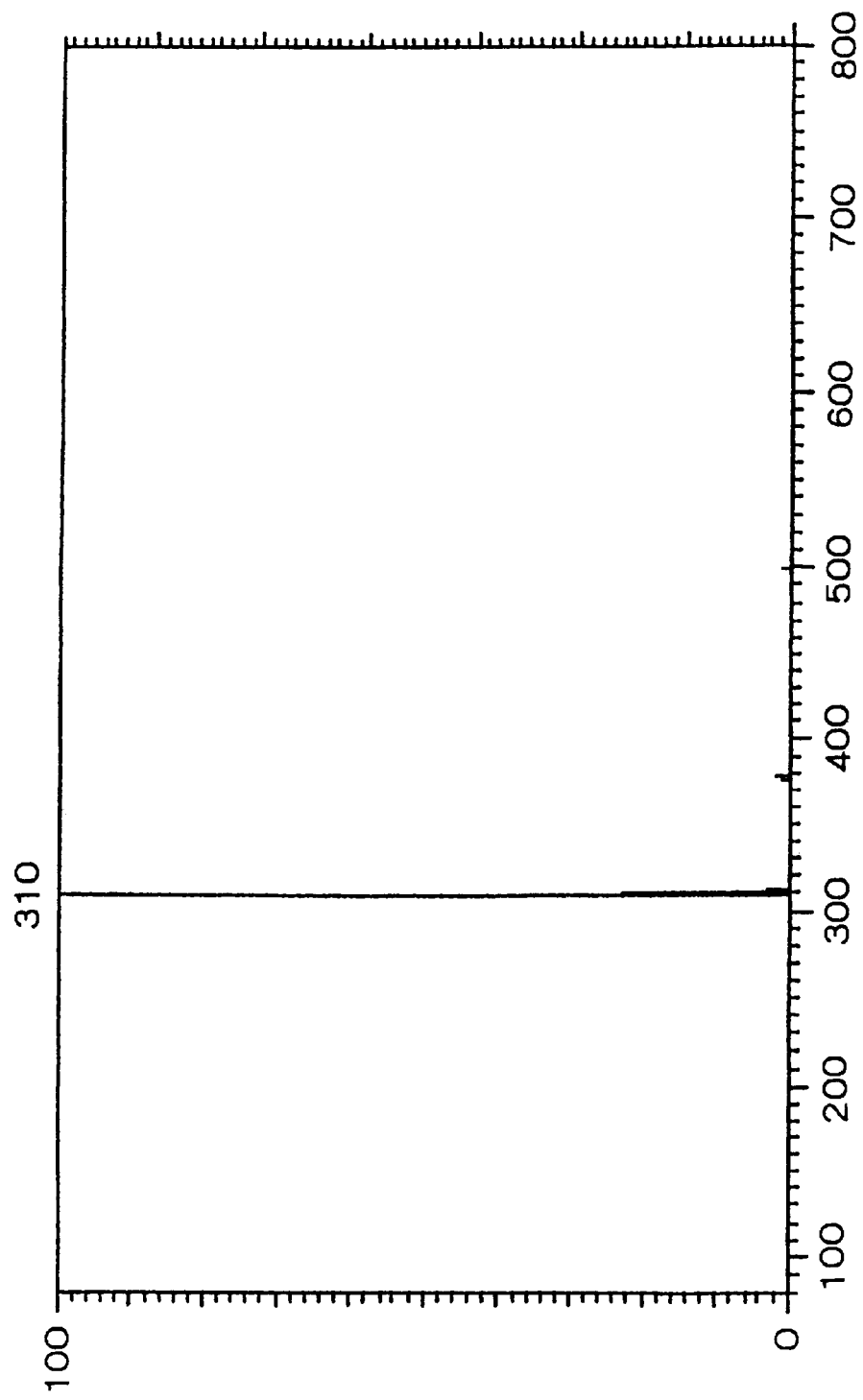
FIG. 3 shows an FD-MS spectrum of the compound IV.

The results of analysis by GPC of 1,3-bis(4-hydroxy-3,5-dimethylphenyl)cyclopentane thus obtained (called compound IV) are shown in FIG. 2. Its yield determined by GPC was 82% (area ratio). The results of FD-MS of the compound IV obtained are shown in FIG. 3. The results of this mass spectrometry were in agreement with molecular weight 310 derived from the structural formula.

(3) Epoxidation of Compound IV:

Into a 3-liter flask having a stirrer, a condenser and a thermometer, 80 g of the compound IV, 600 g of epichlorohydrin, 300 g of 1,4-dioxane and 80 g of dimethyl sulfoxide (hereinafter "DMSO") were introduced, and 25 g of an aqueous 48% by weight sodium hydroxide solution was added dropwise over a period of 1 hour while stirring the mixture at 65° C. and 650 mmHg of decompression, and thereafter the water in the system was removed, followed by further stirring for 4 hours.

From the reaction solution thus obtained, the solvent used in the reaction and unreacted epichlorohydrin were removed under reduced pressure, followed by addition of 50 ml of MIBK, where washing with water was repeated until the inorganic salt formed and the sodium hydroxide were removed. At the time the washing turned neutral, the MIBK was removed by an evaporator to obtain a glycidyl-etherified compound of the compound IV, 1,3-bis[4-(2,3-epoxypropoxy)-3,5-dimethylphenyl]cyclopentane (called compound V).

(Compound V)

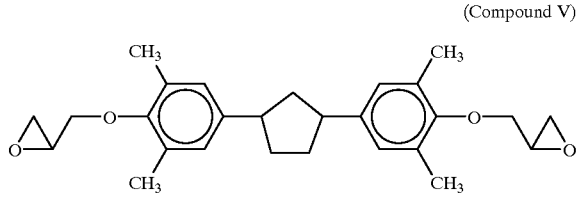

Figure 4:
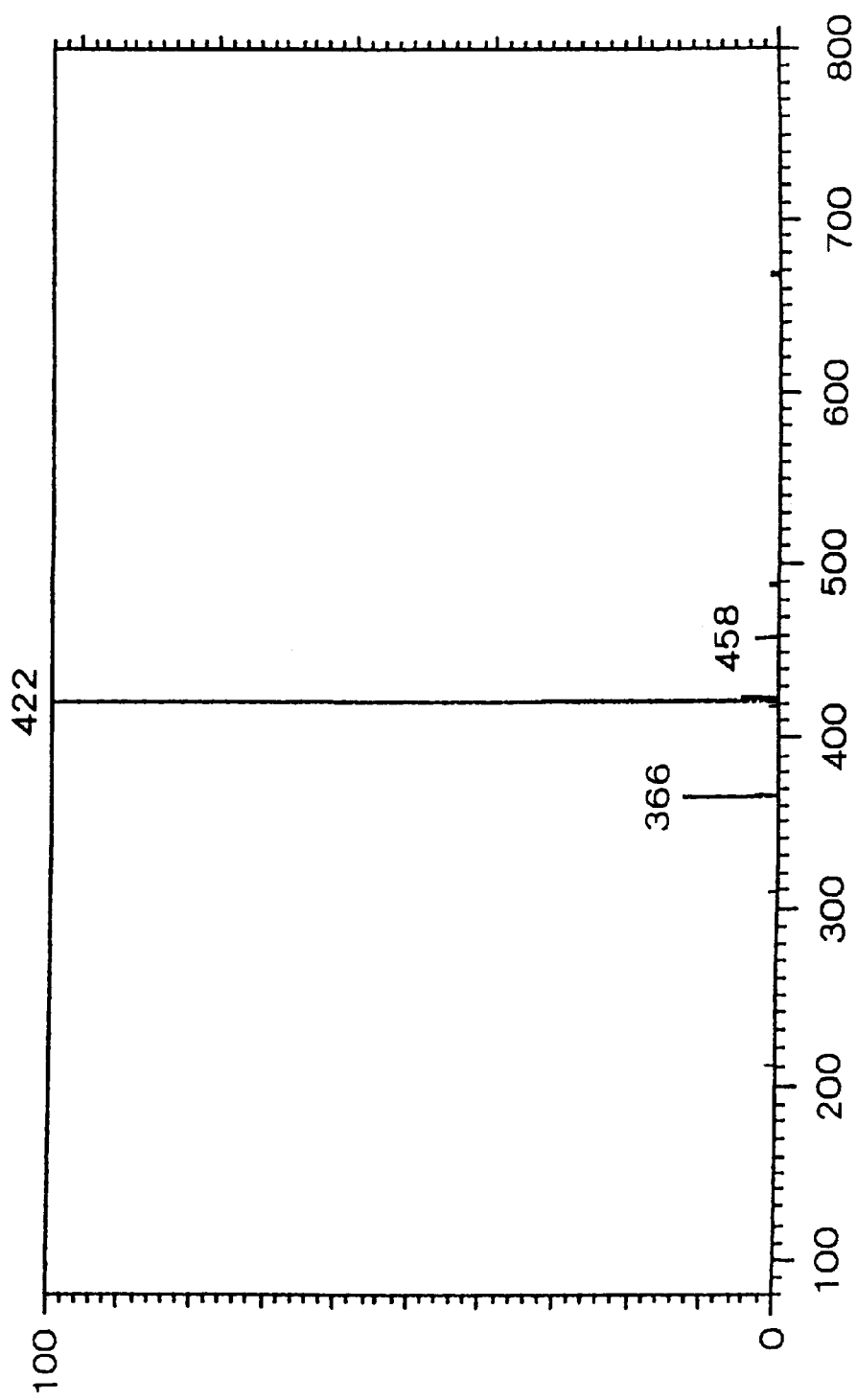
FIG. 4 shows an FD-MS spectrum of compound V.
Figure 5:
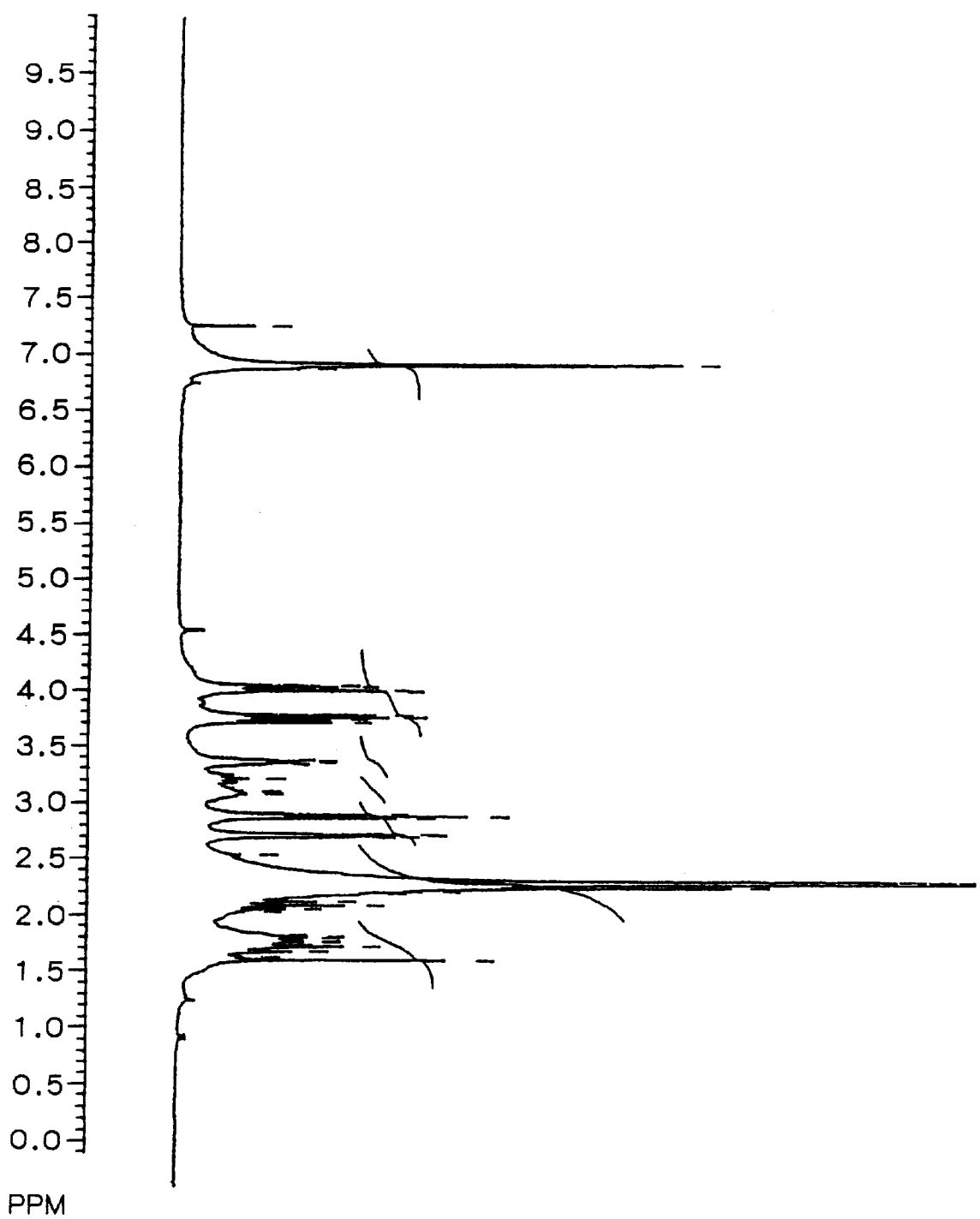
FIG. 5 shows a $^1$H-NMR spectrum of compound V.

FD-MS and NMR spectra of the compound V thus obtained are shown in FIGS. 4 and 5, respectively. Molecular weight 422 of the compound V can be identified from the FS-MS, and the individual functional groups of the compound V can be assigned from the NMR spectrum shown in FIG. 5. Signals of aromatic protons corresponding to 4H are seen around 7 ppm as viewed from the low magnetic field side; proton signals due to the 2,3-epoxypropoxyl group, 4 to 2.5 ppm; and proton signals of the methyl group and cyclopentane ring, at 2.5 to 1.5 ppm. The compound V had an epoxy equivalent of 248.

Synthesis Example 2

(1) Synthesis of 2-Methyl-4-(2-cyclopenten-1-yl) phenol

Figure 6:
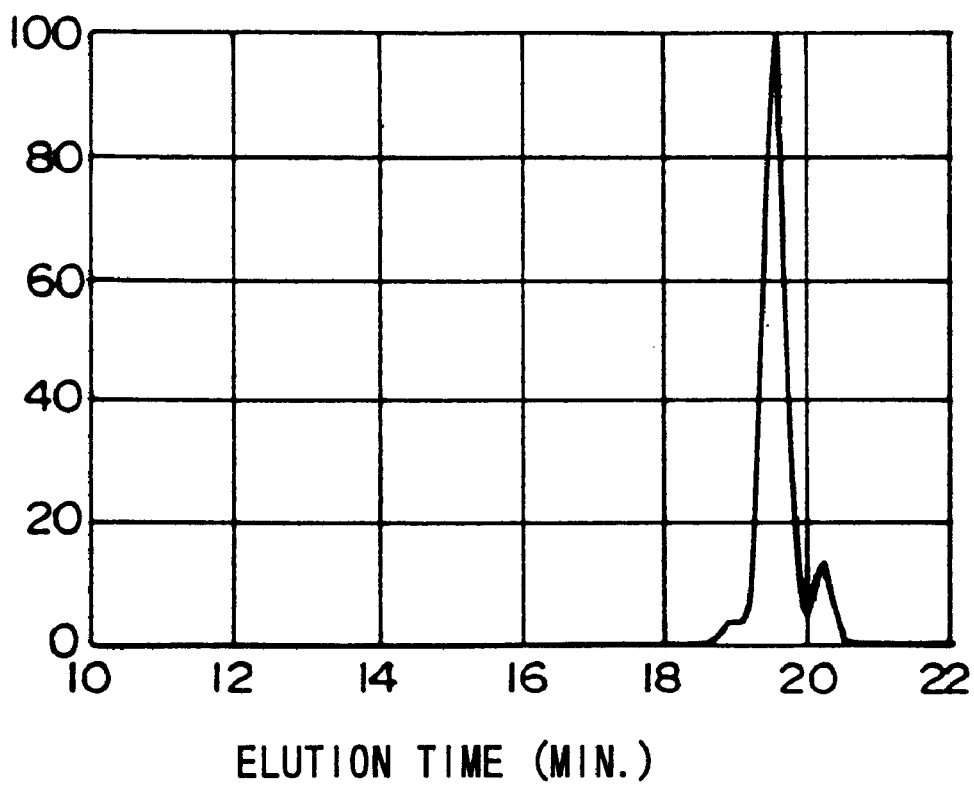
FIG. 6 shows a GPC chromatogram of 2-methyl-4-(2-cyclopenten-1-yl)phenol.

The procedure of Synthesis Example 1-(1) was repeated to synthesize 2-methyl-4-(2-cyclopenten-1-yl)phenol, except that 366 g of 2,6-dimethylphenol was replaced with 324 g of 2-methylphenol, and the toluene, the phosphoric acid and the cyclopentadiene were added in amount of 324 g, 44 g and 198 g, respectively. A fraction at 2 mmHg and 115 to 120°* C. was the intended 2-methyl-4-cyclopentenylphenol. The results of analysis by GPC thereof are shown in FIG. 6. Its yield determined by GPC was 90% (area ratio).

(2) Synthesis of 1,3-Bis(4-hydroxy-3-methylphenyl) cyclopentane (Compound VI)

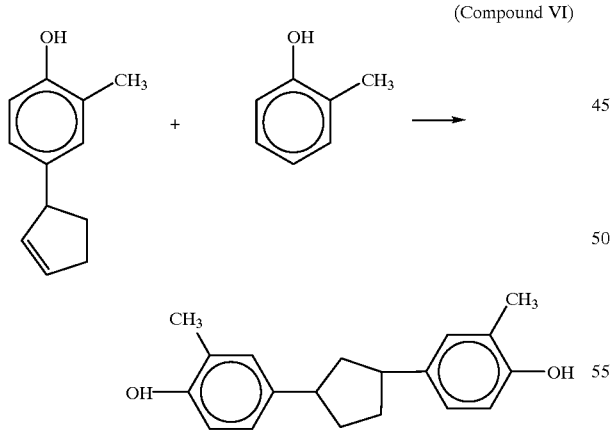

Figure 7:
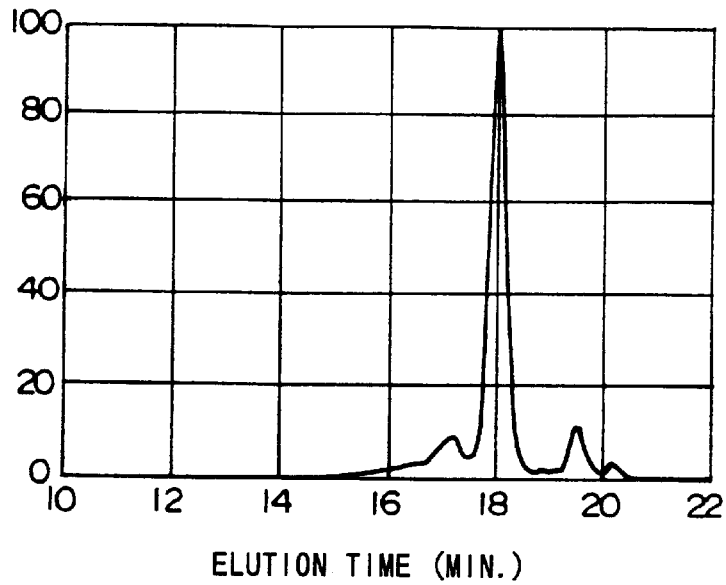
FIG. 7 shows a GPC chromatogram of compound VI.

The procedure of Synthesis Example 1-(2) was repeated to synthesize 1,3-bis(4-hydroxy-3-methylphenyl) cyclopentane (called compound VI), except that the 2,6-dimethylphenol and the PTS were added in amount of 108 g and 10 g, respectively, the mixture solution added dropwise thereto was replaced with a solution of mixture of 34.8 g of 2-methyl-4-(2-cyclopenten-1-yl)phenol and 40 g of toluene, and the reaction time at 80° C. was changed to 8 hours. The results of analysis by GPC thereof are shown in FIG. 7. Its yield determined by GPC was 73% (area ratio).

(3) Epoxidation of Compound VI:

The procedure of Synthesis Example 1-(3) was repeated to obtain 1,3-bis[α4-(2,3-epoxypropoxy)-3-methylphenyl] cyclopentane (called compound VII), except that the compound IV was replaced with the compound VI.

(Compound VII)

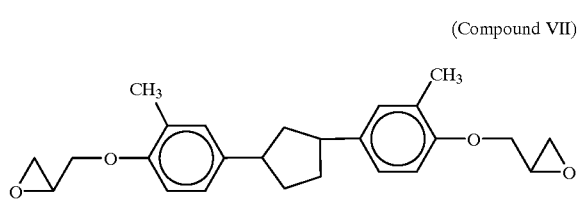

Figure 8:
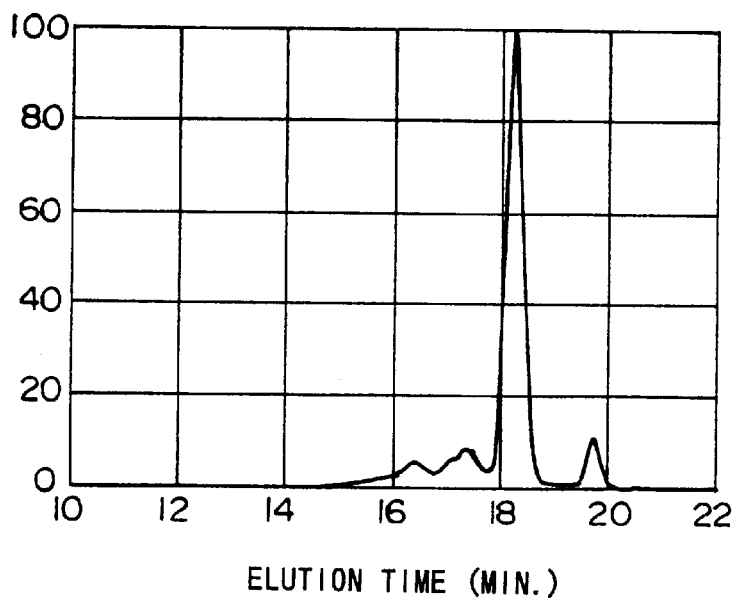
FIG. 8 shows a GPC chromatogram of compound VII.
Figure 9:
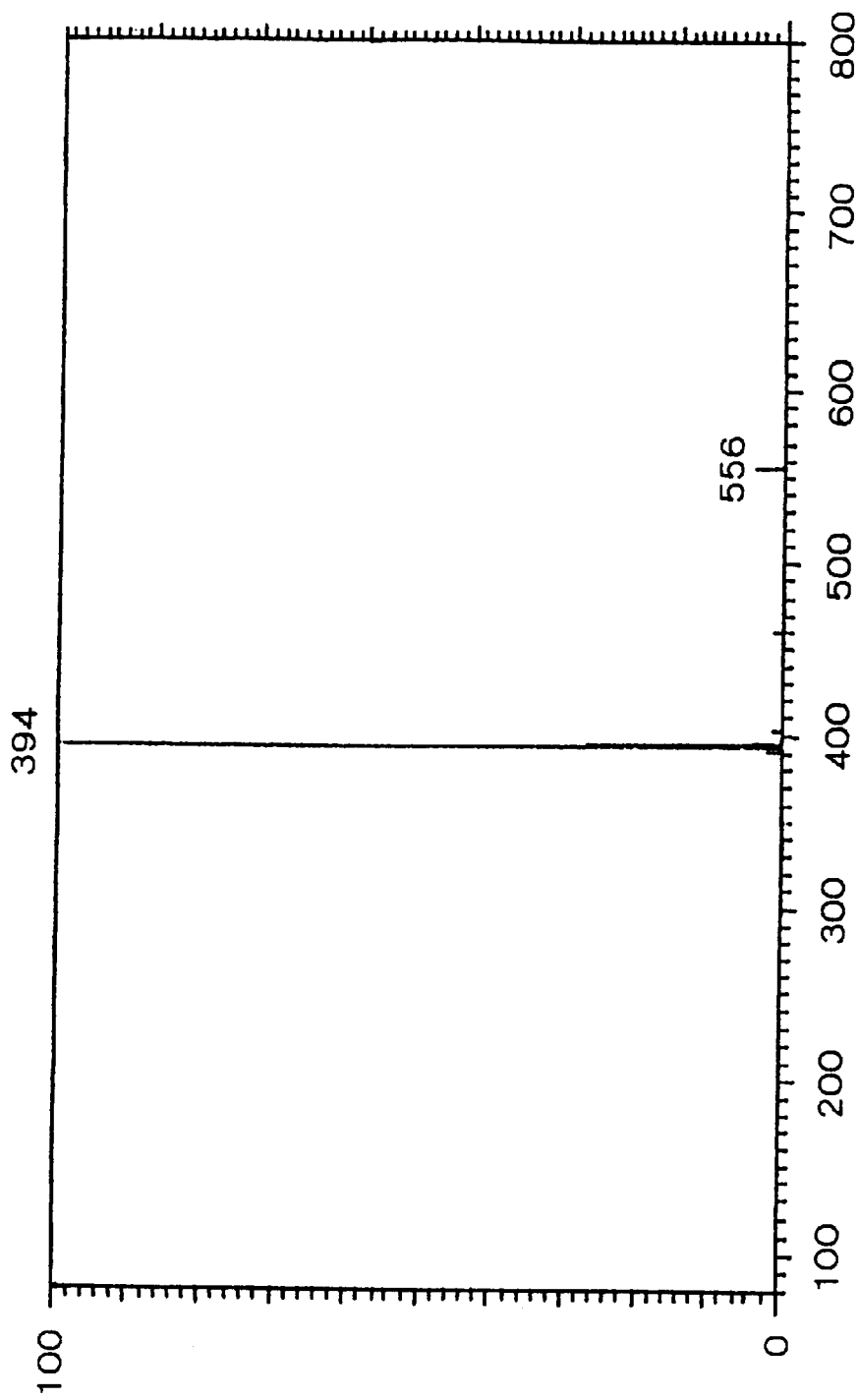
FIG. 9 shows an FD-MS spectrum of the compound VII.
Figure 10:
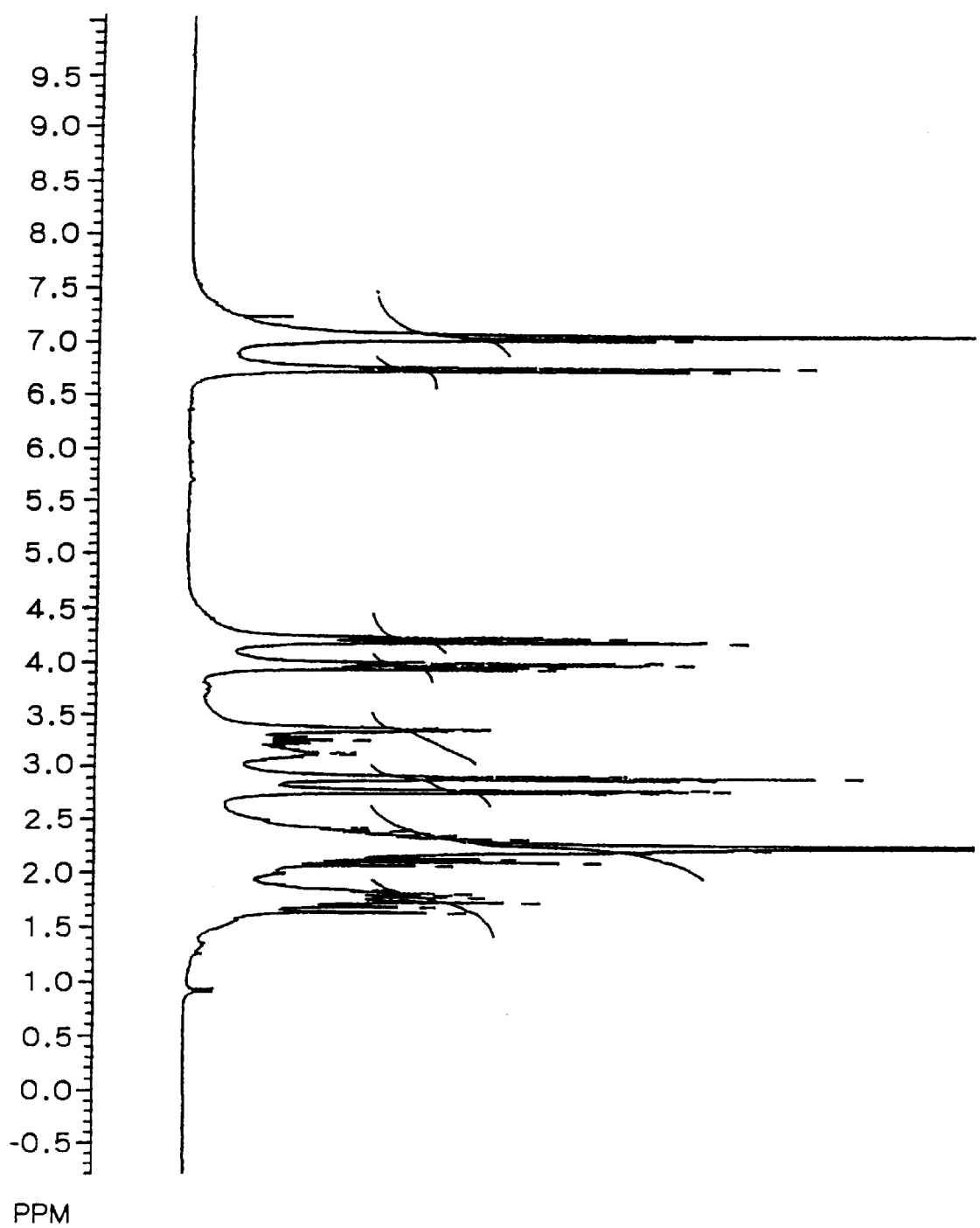
FIG. 10 shows a $^1$H-NMR spectrum of the compound VII.

The GPC chromatogram, FD-MS and NMR spectra of the compound VII thus obtained are shown in FIGS. 8, 9 and 10, respectively. Its yield determined from the GPC chromatogram was 71%. Molecular weight 394 of the compound VII can be identified from the FD-MS, and the individual functional groups of the compound VII can be assigned from the NMR spectrum shown in FIG. 6. Signals of aromatic protons are seen around. 7 ppm as viewed from the low magnetic field side; proton signals due to the 2,3-epoxypropoxyl group, 4.4 to 2.7 ppm; and proton signals of the methyl group and cyclopentane ring, at 2.6 to 1.6 ppm. The compound VII had an epoxy equivalent of 224.

Synthesis Example 3

(1) Synthesis of 1-(2-Cyclopenten-1-yl)-2-naphthol

Figure 11:
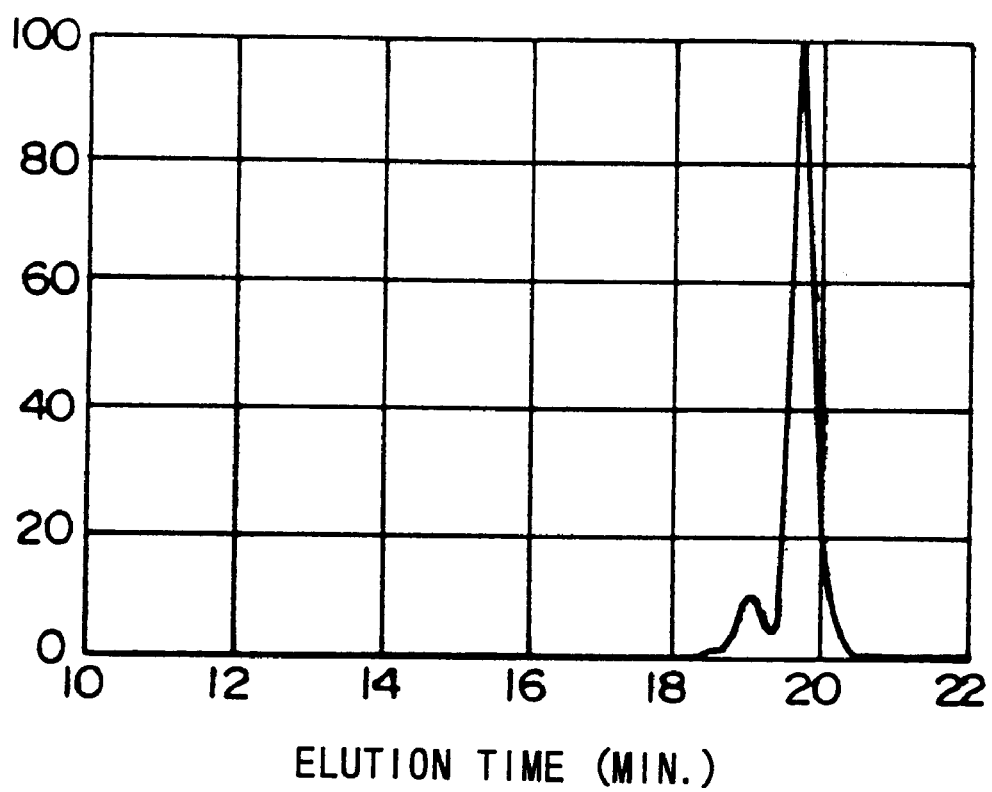
FIG. 11 shows a GPC chromatogram of 1-(2-cyclopenten-1-yl)-2-naphthol.
Figure 12:
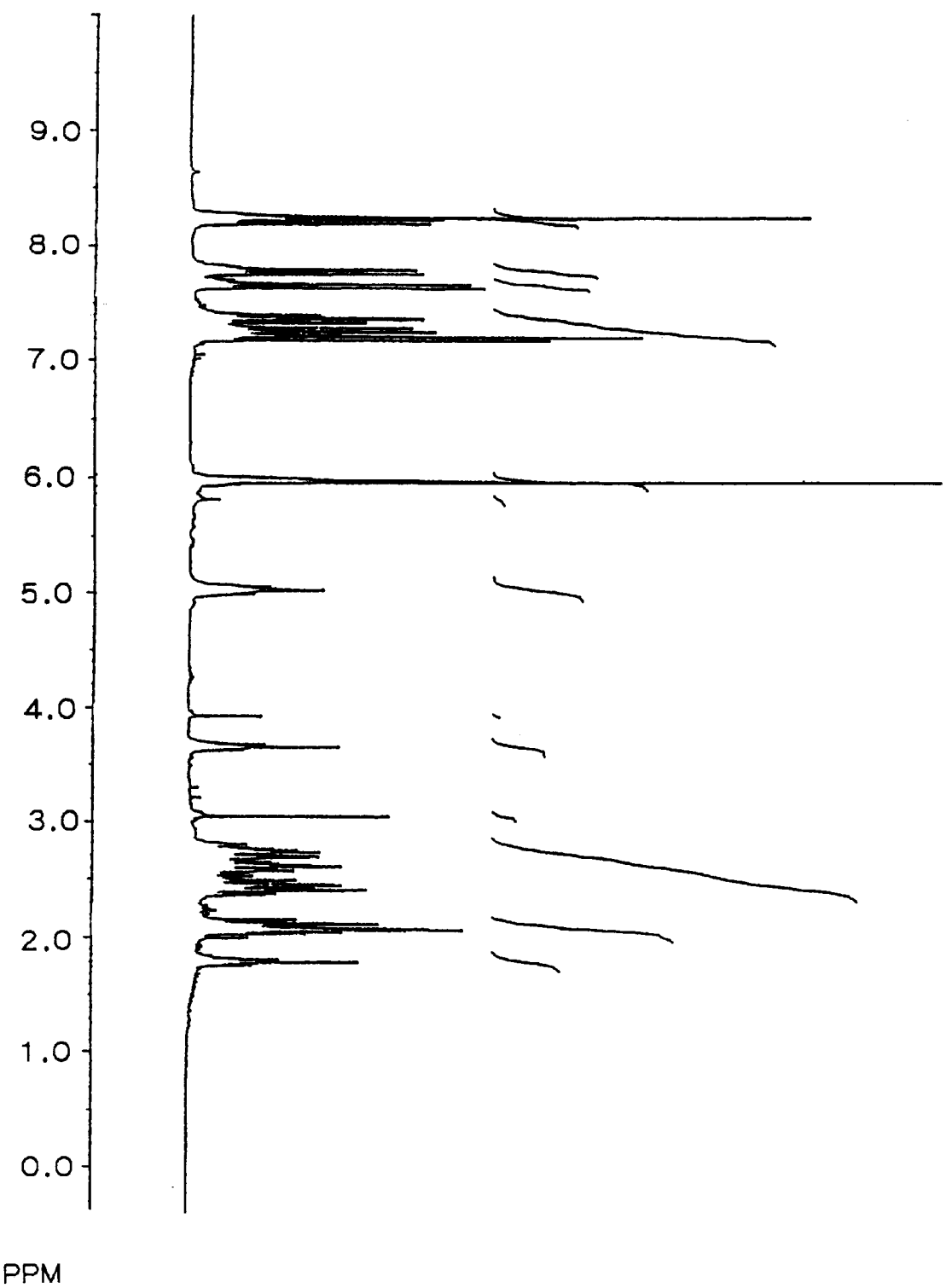
FIG. 12 shows a $^1$H-NMR spectrum of the 1-(2-cyclopenten-1-yl)-2-naphthol.

Into a 2-liter flask having a stirrer, a condenser and a thermometer, 144 g of 2-naphthol, 200 g of methanol and 40 g of PTS were introduced, and a solution of mixture of 66 g of cyclopentadiene and 60 g of methanol was added dropwise over a period of 3 hours while stirring the mixture at room temperature, followed by further stirring for 4 hours at room temperature. To the reaction solution thus obtained, THF and MIBK were added, and the resultant solution was washed with 200 ml of an aqueous 10% sodium hydroxide solution five times, and thereafter further washed with water until it turned neutral, followed by removal of the solvent using an evaporator. The results of analysis by GPC thereof are shown in FIG. 11. Its yield determined by GPC was 90% (area ratio). An NMR spectrum of the 1-(2-penten-1-yl)-2-naphthol obtained is shown in FIG. 12.

(2) Synthesis of 2-Hydroxy-1-[3-(4-hydroxy-3,5-imethylphenyl)cyclopentyl]naphthalene (Compound VIII)

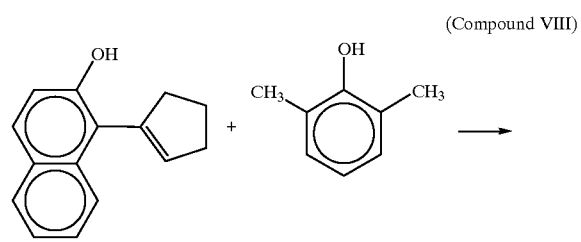

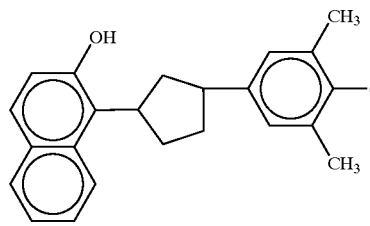

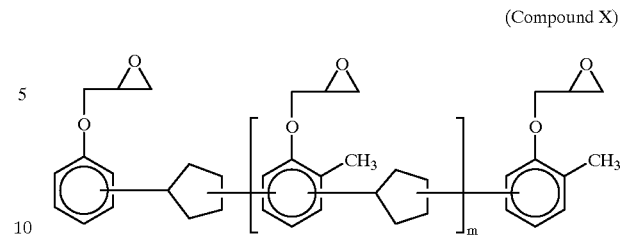

(Compound X)

Figure 13:
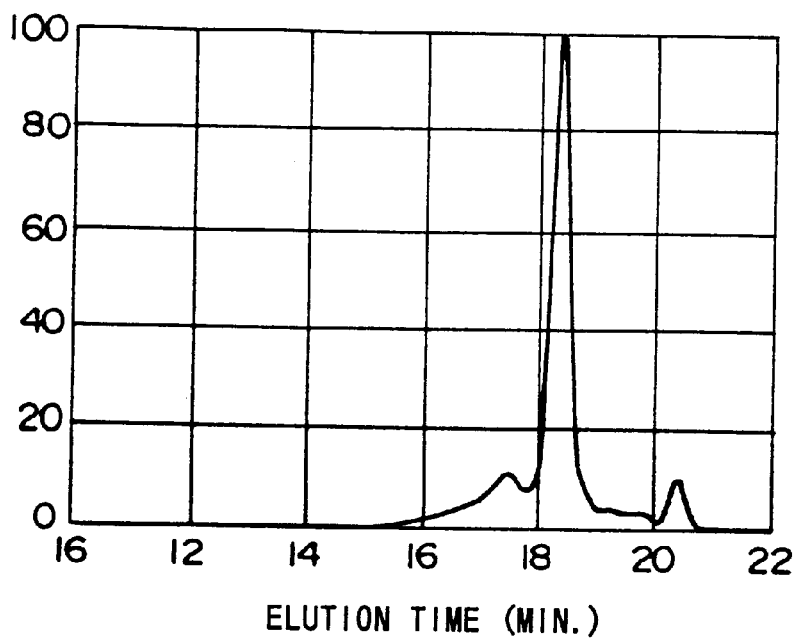
FIG. 13 shows a GPC chromatogram of compound VIII.

The procedure of Synthesis Example 1-(2) was repeated to synthesize the intended 2-hydroxy-1-[3-(4-hydroxy-3,5-dimethylphenyl)cyclopentyl]naphthalene (called compound VIII), except that the 2,6-dimethylphenol was added in amount of 280 g, the mixture solution added dropwise thereto was replaced with a solution of mixture of 120 g of 1-(2-cyclopenten-1-yl)-2-naphthol and 120 g of toluene, and the time of addition was changed to 2 hours. The results of analysis by GPC thereof are shown in FIG. 13. Its yield determined by GPC was 72% (area ratio).

Synthesis Example 4

(1) Polymerization of 2-Methyl-4-(2-cyclopenten-1-yl)phenol

Figure 14:
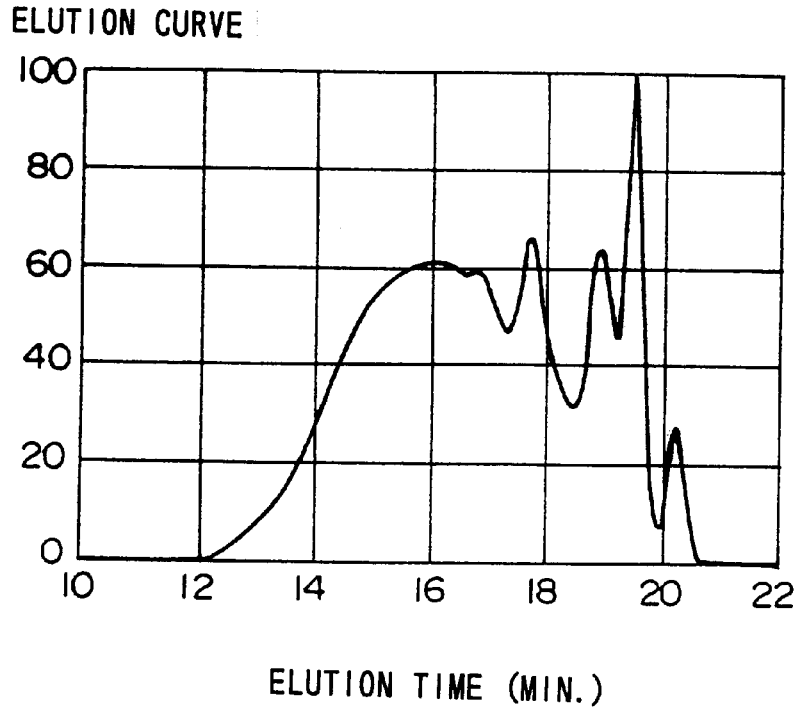
FIG. 14 shows a GPC chromatogram of compound IX.

Into a 2-liter flask having a stirrer, a condenser and a thermometer, 174 g of 2-methyl-4-(2-cyclopenten-1-yl)phenol, 27 g of 2-methylphenol and 10 g of PTS were introduced, and the mixture obtained was stirred for 4 hours while keeping it at 110° C. Next, the reaction solution obtained was cooled, and MIBK was added thereto to make the resin dissolve. Thereafter, in order to remove acid, the resultant solution was washed with water until it turned neutral, followed by removal of the solvent and unreacted monomers using an evaporator to obtain a polymer (called compound IX) having a softening point of 81° C. and a number-average molecular weight of 450. The results of analysis by GPC thereof are shown in FIG. 14.

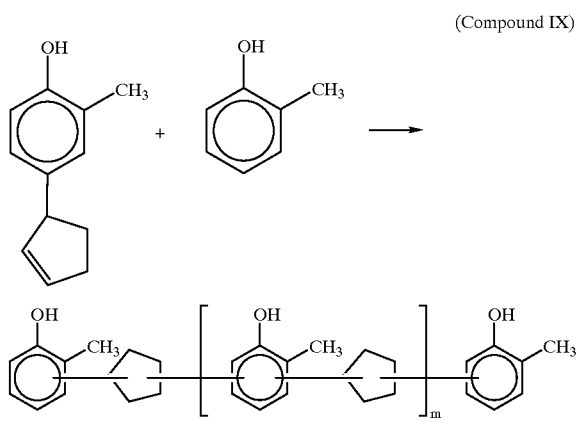

(Compound IX)

(2) Epoxidation of Compound IX

The procedure of Synthesis Example 1-(3) was repeated to obtain a glycidyl-etherified compound of the compound IV (called compound X), except that the compound IX was replaced with 90 g of the compound IX and the aqueous sodium hydroxide solution was added dropwise in amount of 30 g. The compound X thus obtained showed a fluidity at room temperature and had an epoxy equivalent of 280.

Synthesis Example 5

Figure 15:
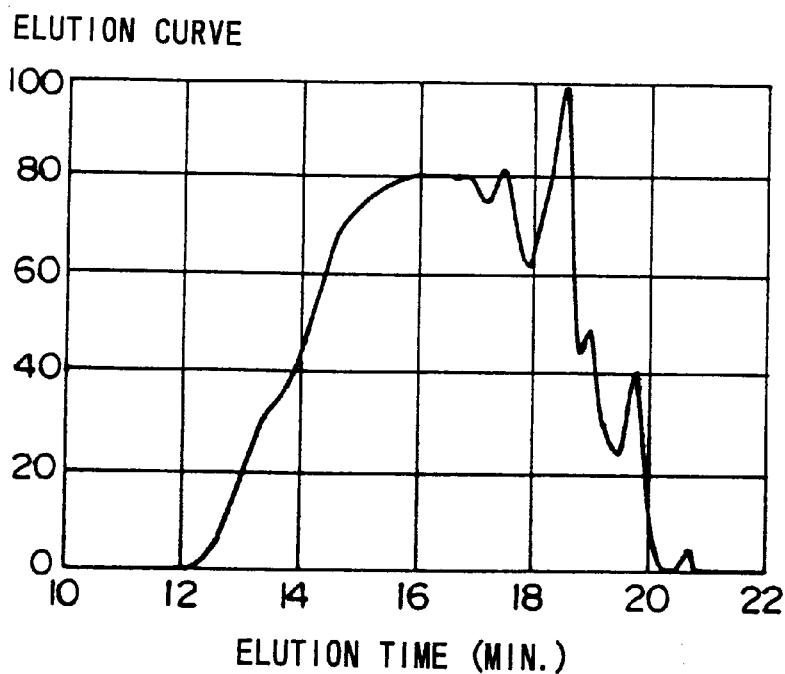
FIG. 15 shows a GPC chromatogram of compound XI.

(1) Polymerization of 4-(2-cyclopenten-1-yl)phenol:

The procedure of Synthesis Example 4-(1) was repeated except that the starting materials were replaced with 160 g of 4-(2-cyclopenten-1-yl)phenol, 9.4 g of phenol and 5 g of PTS, thus a polymer (called compound XI) having a softening point of 85° C. and a number-average molecular weight of 672 was obtained. The results of analysis by GPC thereof are shown in FIG. 15.

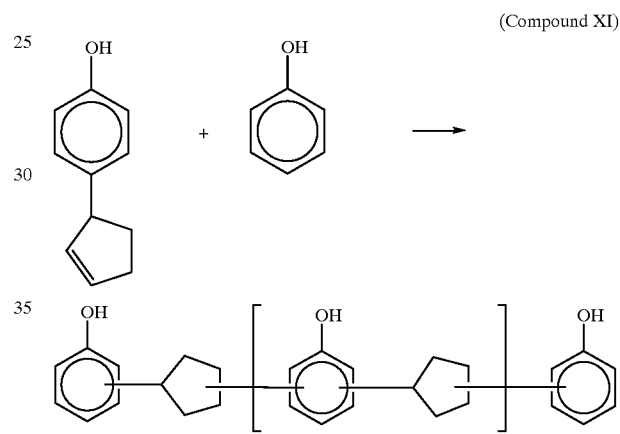

(Compound XI)

(2) Epoxidation of Compound XI:

The procedure of Synthesis Example 4-(2) was repeated to obtain a glycidyl-etherified compound of the compound XI (called compound XII), except that the compound IX was replaced with the compound XI. The compound XII thus obtained was an epoxy resin having a softening point of 65° C. and an epoxy equivalent of 290.

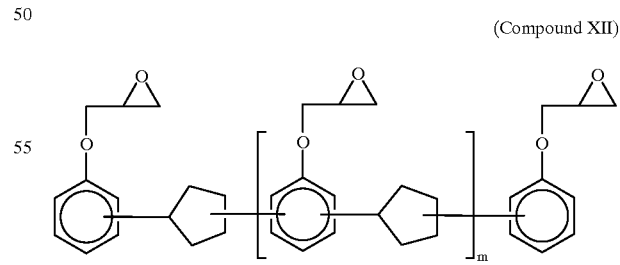

(Compound XII)

Synthesis Example 6

(1) Polymerization of 1-(2-cyclopenten-1-yl)-2-hydroxynaphthalene:

Into a 2-liter flask having a stirrer, a condenser and a thermometer, 72 g of 1-naphthol and 10 g of PTS were introduced, and a solution of mixture of 105 g of (2-cyclopenten-1-yl)-2-hydroxynaphthalene and 105 g of toluene was added dropwise over a period of 1 hour while stirring and keeping the mixture at 100° C., followed by further stirring for 4 hours.

Figure 16:
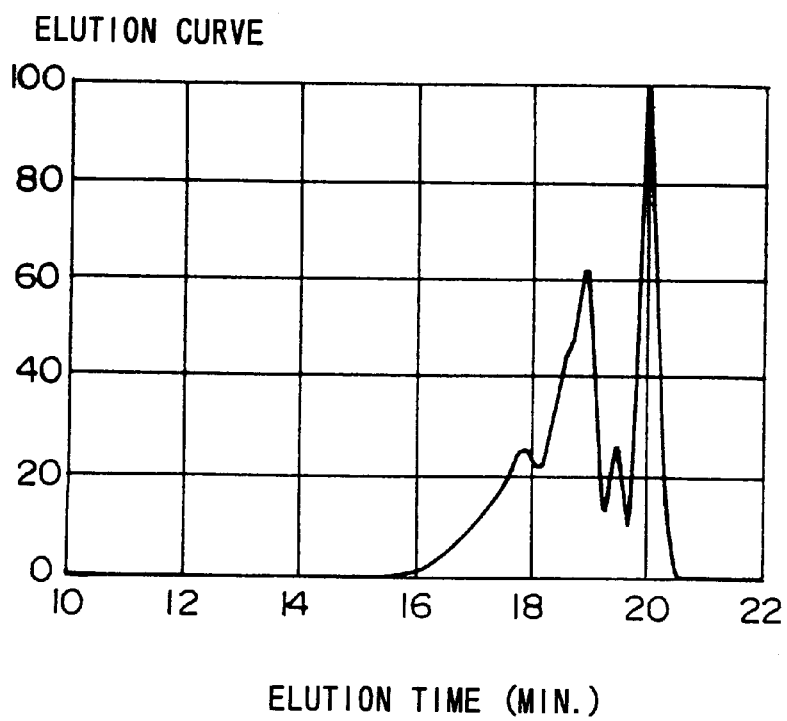
FIG. 16 shows a GPC chromatogram of compound XIII.

Next, to the reaction solution obtained, 500 ml of MIBK was added to make it dissolve, and the resultant solution was washed with 200 ml of an aqueous 10% sodium hydroxide solution five times, and thereafter washed with water until it turned neutral, followed by removal of the solvent from the organic layer using an evaporator to obtain a resin (compound XIII). The results of analysis by GPC thereof are shown in FIG. 16. The resin thus obtained has an average molecular weight of 250.

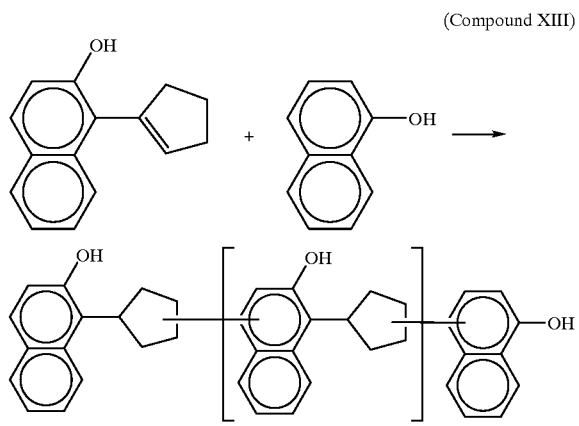

(Compound XIII)

Synthesis Example 7

(1) Synthesis of (2-Cyclopenten-1-yl)-1-naphthol

The procedure of Synthesis Example 3-(1) was repeated to obtain a mixture of 2-(2-cyclopenten-1-yl)-1-naphthol and 4-(2-cyclopenten-1-yl)-1-naphthol, except that the starting material 2-naphthol was replaced with 1-naphthol.

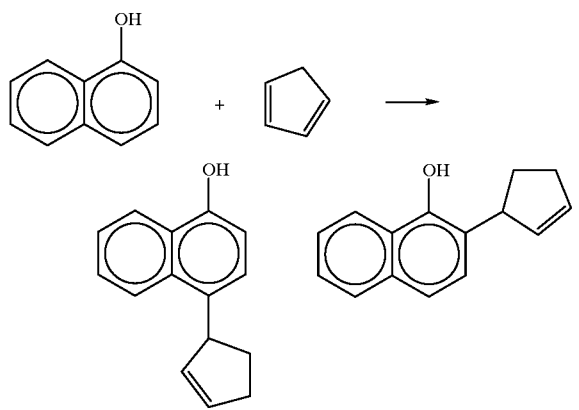

(2) Copolymerization of 2-methyl-4-(2-cyclopenten-1-yl) phenol with 1-(2-cyclopenten-1-yl)-2-hydroxynaphthalene:

Into a 2-liter flask having a stirrer, a condenser and a thermometer, 121 g of (2-cyclopenten-1-yl)-1-naphthol obtained in (1), 100 g of 2-methyl-4-(2-cyclopenten-1-yl) phenol and 2 g of PTS were introduced, and the mixture obtained was stirred for 2 hours while keeping it at 110° C. Next, the reaction solution obtained was put into a vat made of stainless steel and then cooled to solidify, followed by pulverization. The pulverized product was dissolved in acetone, the solution obtained was poured into water to effect reprecipitation to remove the PTS used as a catalyst, further followed by solubility fractionation using acetone/n-hexane (volume ratio: 1/4) to remove unreacted matter, thus a cooligomer (called compound XIV) having a softening point of 87° C. and a number-average molecular weight of 520 was obtained.

The cooligomer (called compound XIV) thus obtained was a random copolymer having a repeating unit represented by the following structural formula XIVa and a repeating unit represented by the following structural formula XIVb and a copolymerization ratio (i.e., the ratio of the number of the repeating unit XIVa to the number of the repeating unit XIVb in one molecule) of 1:1.

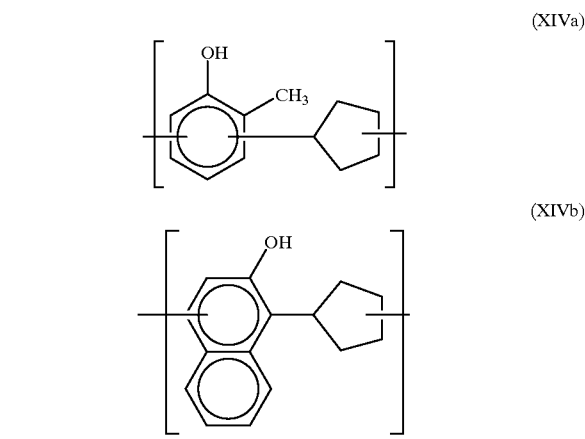

Figure 17:
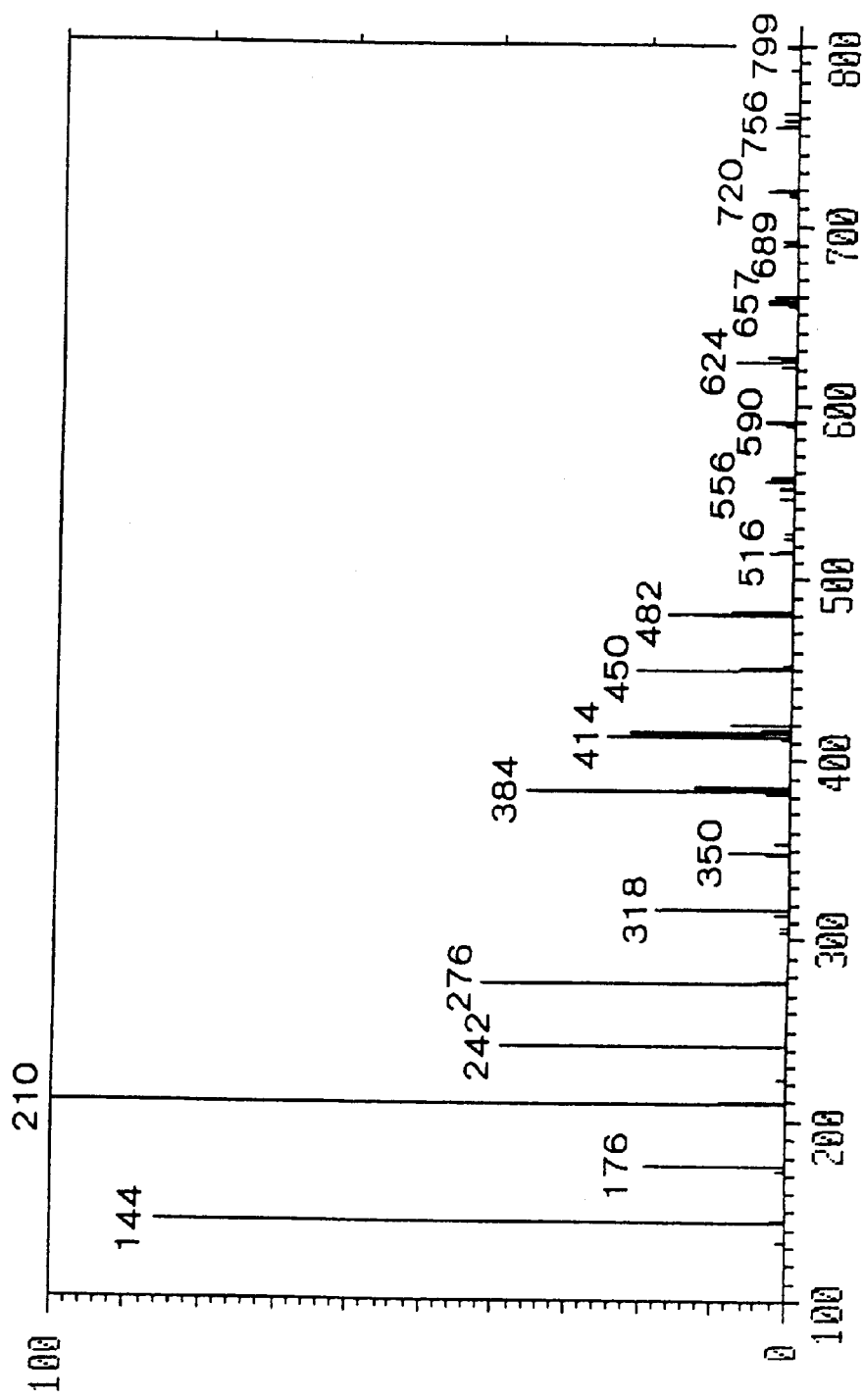
FIG. 17 shows an FD-MS spectrum of compound XIV.
Figure 18:
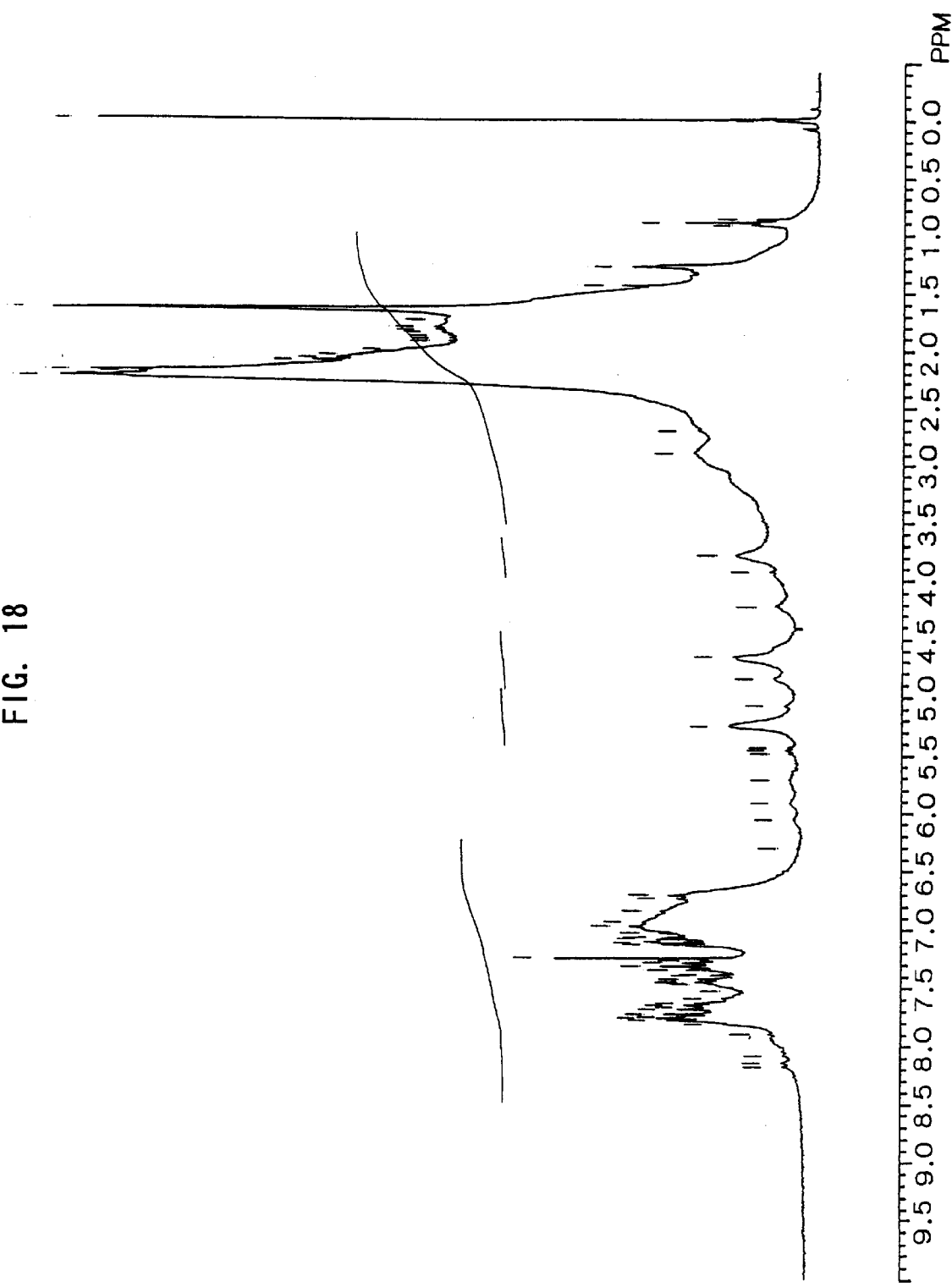
FIG. 18 shows a $^1$H-NMR spectrum of the compound XIV.
Figure 19:
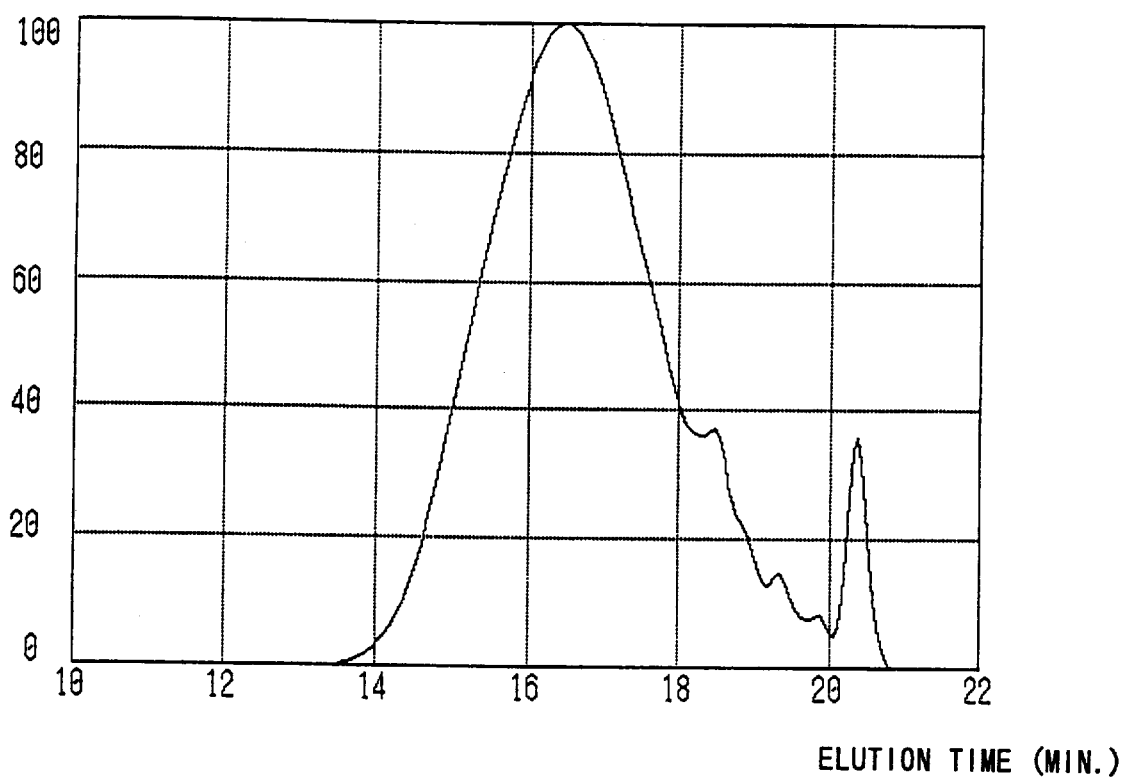
FIG. 19 shows a GPC chromatogram of compound XIV.

The FD-MS spectrum, $^1$H-NMR spectrum and GPC chromatogram of the compound XIV thus obtained are shown in FIGS. 17, 18 and 19, respectively.

Examples 1 & 2, Comparative Examples 1 & 2

Using the compound V obtained in Synthesis Example 1-(3) and the compound XIII obtained in Synthesis Example 6-(1), the melt viscosity of the epoxy resin and modified phenol resin of the present invention was measured to compare it with that of conventional products. The results are shown in Table 1 below.

TABLE 1

| | Epoxy resin | | Modified phenol resin | |
| --- | --- | --- | --- | --- |
| | Example 1 | Comparative Example 1 | Example 2 | Comparative Example 2 |
| Compound: | Compound V | Comparative resin 1 | Compound XIII | Comparative resin 2 |
| Viscosity: | 0.05 | 0.1 | 0.1 | 20 |

Viscosity: poise

The comparative resin 1 is YX-4000H, available from Yuka Shell Epoxy K.K., and the comparative resin 2 is NH-7000, available from Nippon Kayaku Co., Ltd. Structural formulas of these compounds are shown below.

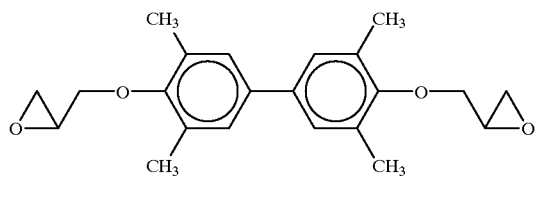

(Comparative resin 1)

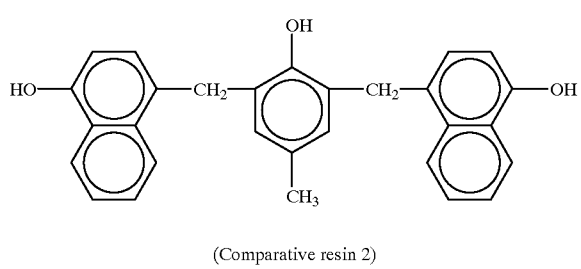

(Comparative resin 2)

The viscosity is melt viscosity after 1-minute leaving, measured using an ICI cone plate viscometer, manufactured by PEL Co. The viscosity of 0.1 to 0.3 g of the resin put on a hot plate is measured after one minute leaving under the condition of a measuring temperature of 150° C. in the state that the cone is lowered.

As can be seen from the above Table 1, the compounds V and XIII of the present invention both have a lower melt viscosity than that of conventional products having similar structure, and have a good fluidity. Hence, they are advantageous as molding materials for encapsulating electronic devices.

Example 3, Comparative Examples 3 & 4

To compare the modified phenol resin obtained in Synthesis Example 4-(1) with conventional products, resin compositions were prepared using various resins as epoxy resin curing agents and using ESCN-190 (an orthocresol novolak epoxy resin having an epoxy equivalent of 195), available from Sumitomo Chemical Co., Ltd., as epoxy resin, and were cured. The rate of moisture absorption of the cured products was measured.

First, the epoxy resin ESCN-190, the epoxy resin curing agent in an amount of 1 equivalent based on the epoxy groups of this epoxy resin and a curing accelerator (SA-841, available from SAN-APRO LIMITED) in an amount of 6 parts by weight based on 100 parts by weight of the epoxy resin were mixed. The mixtures obtained were each pulverized for 30 minutes by means of an automated mortar, thus epoxy resin compositions were prepared.

The epoxy resin compositions thus obtained were held between stainless steel mirror plates, and were press-molded under conditions of 140° C., 30 minutes and 3 MPa, followed by post-curing treatment under conditions of 175° C. and 5 hours to produce test resin plates of 2 mm thick. Test pieces of 50 mm diameter were cut out, and their rates of moisture absorption in 72 hours and 168 hours were measured under conditions of 85° C. /85%RH. The epoxy resin curing agents used and the results of measurement are shown in Table 2 below.

TABLE 2

| | Example 3 | Comparative Example 3 | Comparative Example 4 |
|---|---|---|---|
| Curing agent: | Compound XI | Comparative resin 3 | Comparative resin 4 |
| Epoxy resin: | | ESCN-190 | |
| Rate of moisture absorption: (% by weight) | | | |
| 72 hours: | 0.763 | 1.19 | 0.873 |
| 168 hours: | 1.096 | 1.665 | 1.218 |

The comparative resin 3 is H-1 (phenol novolak resin), available from Meiwa Chemical Plastic Industry, Ltd., and the comparative resin 4 is DPP-M (phenol resin having tricyclo[5.2.1.0$^{2,6}$] decylene group in the backbone structure), available from Nippon Oil Co., Ltd. Structural formulas of these compounds are shown below.

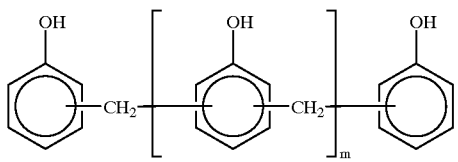

(Comparative resin 3)

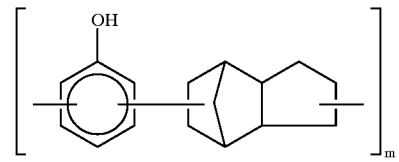

(Comparative resin 4)

Examples 4 to 7, Comparative Examples 5 & 6

(1) Preparation of Epoxy Resin Compositions

Example 4

80 parts by weight of an orthocresol novolak epoxy resin having an epoxy equivalent of 200 and a softening point 73° C., 20 parts by weight of a bromobisphenol A epoxy resin having a bromine percentage of 50% by weight and an epoxy equivalent of 375, 69 parts by weight of the compound XI (softening point: 81° C.; number-average molecular weight: 450; hydroxyl group equivalent: 152) obtained in Synthesis Example 4-(1), 1.5 parts by weight of triphenylphosphine, 3 parts by weight of carnauba wax, 1 part by weight of carbon black, 4 parts by weight of γ-glycidoxypropyltrimethoxysilane, and quartz glass powder (75% by weight of the whole composition) were kneaded at 80 to 90° C. for 10 minutes using a kneading machine (a heating roll of 10 inches diameter) to obtain an epoxy resin composition of Example 4.

Example 5

An epoxy resin composition was prepared in the same manner as in Example 4 except that as the epoxy resin curing agent the compound XI was replaced with 80 parts by weight of the compound XIV (softening point: 87° C.; number-average molecular weight: 520; hydroxyl group equivalent: 176).

Example 6

An epoxy resin composition was prepared in the same manner as in Example 4 except that the orthocresol novolak epoxy resin was replaced with a biphenyl skeleton epoxy resin (4,4'-bis(2,3-epoxypropoxy)-3,3'5,5'-tetramethylbiphenyl available from Yuka Shell Epoxy K.K., EPIKOTE YX-4000H) having a melting point of 106° C. and an epoxy equivalent of 188, and the triphenylphosphine was used in an amount of 2.5 parts by weight and the quartz glass powder in an amount of 85% by weight.

Example 7

An epoxy resin composition was prepared in the same manner as in Example 6 except that as the epoxy resin curing agent the compound XI was replaced with 80 parts by weight of the compound XIV (softening point: 87° C.; number-average molecular weight: 520; hydroxyl group equivalent: 176).

Comparative Example 5

An epoxy resin composition was prepared in the same manner as in Example 4 except that as the epoxy resin curing agent the compound XI was replaced with 48 parts by weight of the above comparative resin 3 (a phenol novolak resin having a hydroxyl group equivalent of 106 and a softening point of 83° C.).

Comparative Example 6

An epoxy resin composition was prepared in the same manner as in Example 6 except that as the epoxy resin curing agent the compound XI was replaced with 51 parts by weight of the comparative resin 3.

(2) Production of Resin-encapsulated Electronic Device

Using as molding materials the epoxy resin compositions obtained as described above, resin-encapsulated electronic devices were produced.

Figure 20:
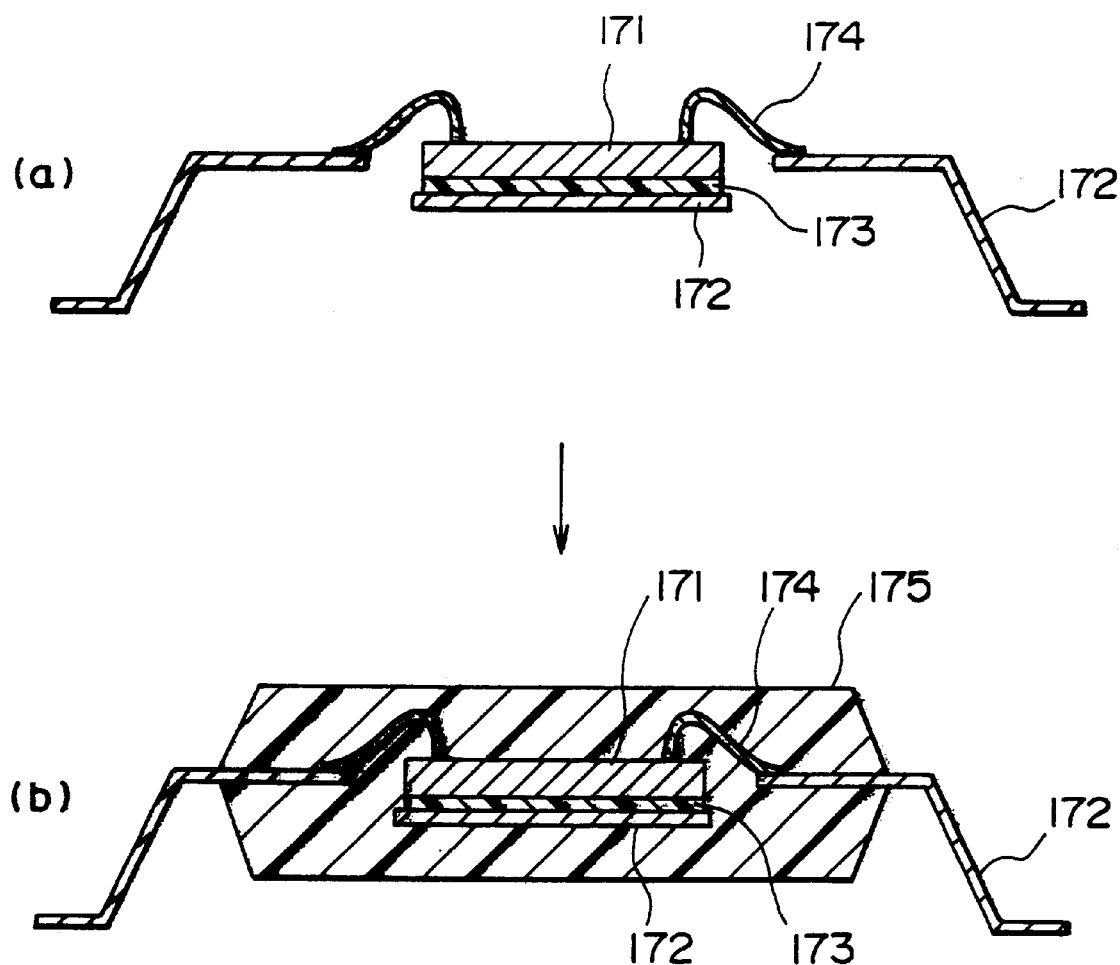
FIG. 20 is a cross-sectional view showing the steps of encapsulating a resin-encapsulated electronic device.

A test silicon chip 171 of 8×10×0.4 mm was bonded onto a lead frame 172 with use of an adhesive 173, and bonding pads of the IC chip 171 and the lead frame 172 were connected by wire bonding through gold wires 174 [FIG. 20(*a*)].

Next, using each of the epoxy resin compositions, transfer molding was so performed as to cover the whole chip 171 to form an encapsulated member 175. Thus, a 80-pin flat package of 20×14×2.7 mm in external dimension was obtained, which was as shown in FIG. 20(*b*).

The transfer molding was performed by molding the resin composition under conditions of 180±3° C., 6.9±0.17 MPa and 90 seconds by a transfer press, followed by post-curing treatment under conditions of 180±5° C. and 5 hours.

(3) Measurement and Evaluation of Properties

On the epoxy resin compositions and electronic devices obtained in the above (1), their properties were measured and evaluated to obtain the results shown in Table 3. As can be seen from the results, the epoxy resin compositions of all Examples, in either case of the cresol novolak epoxy resin and the biphenyl epoxy resin, show higher bond strength and smaller water absorption than the resin compositions of Comparative Examples 1 and 2, in which conventional phenol novolak resins are used as curing agents, and are consequently greatly improved in solder resistance (reflow resistance). The resin compositions of all Examples also show good spiral flow values which are indexes of fluidity, and are seen to have superior fluidity.

TABLE 3

| Properties | Cresol novolak epoxy resin molding material | | | Biphenyl epoxy resin molding material | | |
| --- | --- | --- | --- | --- | --- | --- |
| | Example 4 | Example 5 | Comparative Example 5 | Example 6 | Example 7 | Comparative Example 6 |
| Curing agent: | Compound XI | Compound XIV | Comparative resin 3 | Compound XI | Compound XIV | Comparative resin 3 |
| Spiral flow: (inches) | 42 | 40 | 31 | 45 | 42 | 34 |
| Bond strength: (room temp.) (N/m) | 510 | 600 | 340 | 870 | 910 | 650 |
| Water absorption (72 hrs) (%) | 1.85 | 1.72 | 2.24 | 1.13 | 1.02 | 1.33 |
| Reflow resistance: 48 hrs: (cumulative number of defects/parameter) | 0/10 | 0/10 | 5/10 | 0/10 | 0/10 | 0/10 |
| 72 hrs: | 0/10 | 0/10 | 10/10 | 0/10 | 0/10 | 3/10 |
| 96 hrs: | 8/10 | 5/10 | 10/10 | 0/10 | 0/10 | 7/10 |

The property values shown in Table 3 were measured in the following way.

a. Spiral Flow

Flow length was measured according to ASTM (American Society for Testing and Materials) D3123 under conditions of 180±3° C. and 6.9±0.17 MPa.

b. Bond Strength

The resin composition was spread over an aluminum foil of 50 μm thick and 10 mm wide, and was molded under conditions of 180±3° C., 6.9±0.17 MPa and 90 seconds by a transfer press, followed by post-curing treatment under conditions of 180±5° C. and 5 hours. Peal strength of the aluminum foil on a molded product (thickness: 3 mm) in the direction of 90° was determined using a tensile tester.

c. Water Absorption

To form a test piece, the resin composition was molded under conditions of 180±3° C., 6.9±0.17 MPa and 90 seconds by a transfer press with a mold for molding a disk of 50 mm diameter and 3 mm thick, followed by post-curing treatment under conditions of 180±5° C. and 5 hours. The test piece obtained was moistened according to Japanese Industrial Standard JIS-K-6911 under conditions of 85° C. /85%RH, and its weight was measure at intervals of a prescribed time to determine water absorption.

d. Reflow Resistance

The test IC devices produced in the above (2) were each moistened for a prescribed time, and thereafter heated for 90 seconds by 215° C. vapor phase reflowing. Any cracks were observed by microscopic observation to examine the number of defectives per prescribed time.

POSSIBILITY OF INDUSTRIAL APPLICATION

As described above, the cyclopentylene compound and the epoxy resin composition and molding material for encapsulating electronic devices containing the compound, according to the present invention have a high fluidity and a low moisture absorptivity, and hence are suited especially for producing resin-encapsulated electronic devices such as semiconductor devices.

The encapsulating of electronic devices such as ICs and LSIs (large-scale integrated circuits) with use of the epoxy resin molding material for encapsulating electronic devices of the present invention makes it possible to, as demonstrated in Examples, obtain products having superior soldering resistance and moldability, promising a great industrial advantage.

The cyclopentenyl compound according to the present invention is also useful as an intermediate of the above cyclopentylene compound.

What is claimed is:

1. A compound represented by the following general formula (I):

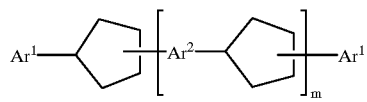

(I)

wherein m represents a positive number; $Ar^1$ represents at least one of monovalent organic groups represented respectively by

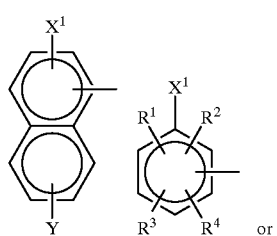

or

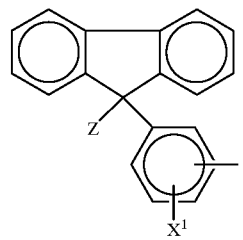

$Ar^2$ represents at least one of divalent organic groups selected from the group consisting of a first atomic group represented by

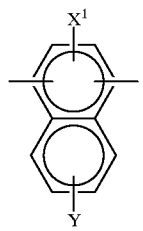

a second atomic group represented by

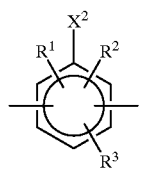

and a third atomic group represented by

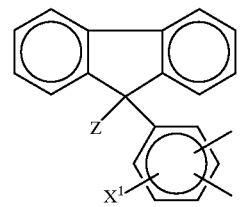

$X^1$ represents a 2,3-epoxypropoxyl group; $X^2$ represents a 2,3-epoxypropoxyl group; Y represents a hydrogen atom, a hydroxyl group or a 2,3-epoxypropoxyl group; Z represents a hydrogen atom, a phenyl group, a hydroxyphenyl group or a 2,3-epoxypropoxyphenyl group; and $R^1$ to $R^4$ are each independently selected from the group consisting of a hydrogen atom, an alkyl group and an aryl group having 1 to 10 carbon atoms and a halogen atom.

2. The compound according to claim 1, wherein the m is not more than 20 on the number average.

3. A compound which is a compound represented by the following general formula (I):

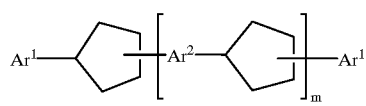

wherein m represents a positive number; Ar¹ represents at least one of monovalent organic groups represented respectively by

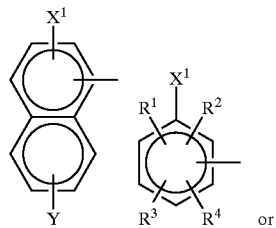

;Ar² represents at least one of divalent organic groups selected from the group consisting of a first atomic group represented by

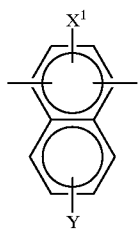

a second atomic group represented by

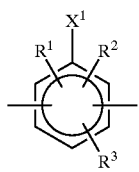

and a third atomic group represented by

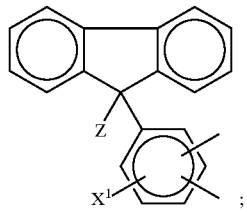

;

$X^1$ represents a 2,3-epoxypropoxyl group; Y represents a hydrogen atom, a hydroxyl group or a 2,3-epoxypropoxyl group; Z represents a hydrogen atom, a phenyl group, a hydroxyphenyl group or a 2,3-epoxypropoxyphenyl group; and $R^1$ to $R^4$ are each independently selected from the group consisting of a hydrogen atom, an alkyl group and an aryl group having 1 to 10 carbon atoms and a halogen atom; and is a cooligomer containing as the groups $Ar^2$ the first atomic group and the second atomic group in one molecule;

the number of said first atomic group and the number of said second atomic group being in a ratio of from 20:1 to 1:20.

4. The compound according to claim 3, which further contains as the group $Ar^2$ the third atomic group in one molecule;

the total number of said first atomic group and second atomic group and the number of said third atomic group being in a ratio of from 9:1 to 8:2.

5. A compound represented by the following general formula (I):

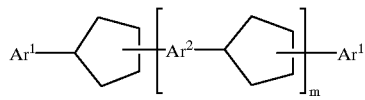

wherein m represents a positive number; Ar¹ represents at least one of monovalent organic groups represented respectively by

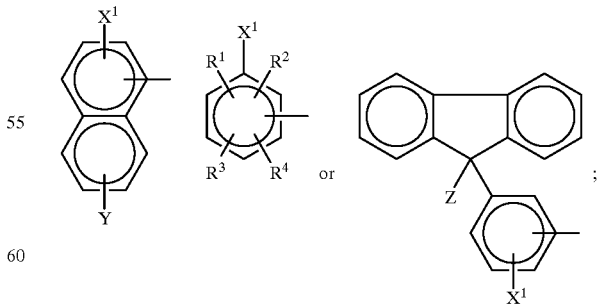

$Ar^2$ represents at least one of divalent organic groups selected from the group selected from a first atomic group represented by

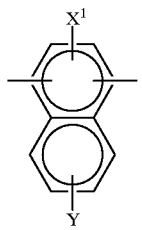

a second atomic group represented by

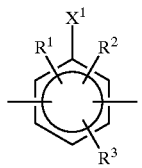

and a third atomic group represented by

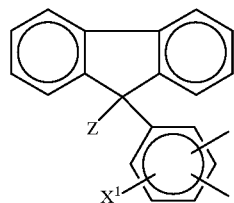

$X^1$ represents a 2,3-epoxypropoxyl group; Y represents a hydrogen atom, a hydroxyl group or a 2,3-epoxypropoxyl group; Z represents a hydrogen atom, a phenyl group, a hydroxyphenyl group or a 2,3-epoxypropoxyphenyl group; and $R^1$ to $R^4$ are each independently selected from the group consisting of selected from a hydrogen atom, an alkyl group and an aryl group having 1 to 10 carbon atoms and a halogen atom; and contains as the groups $Ar^2$ the third atomic group and either the first atomic group or the second atomic group and in one molecule;

the number of said first atomic group or second atomic group and the number of said third atomic group being in a ratio of from 9:1 to 8:2.

6. An epoxy resin molding material for encapsulating electronic devices which comprises at least one of a compound represented by the following general formula (I):

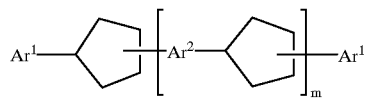

(I)

wherein m represents a positive number; $Ar^1$ represents at least one of monovalent organic groups represented respectively by

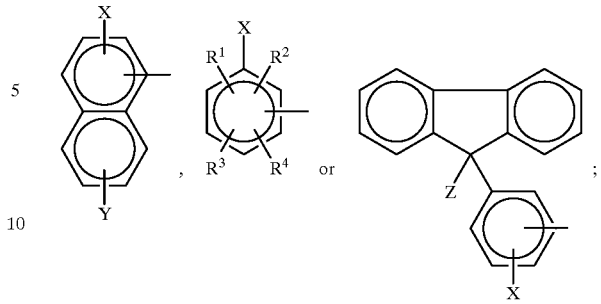

$Ar^2$ represents at least one of divalent organic groups selected from the group consisting of a first atomic group represented by

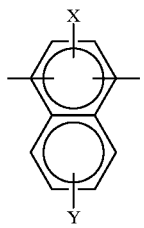

a second atomic group represented by

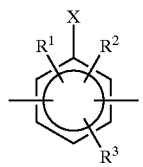

and a third atomic group represented by

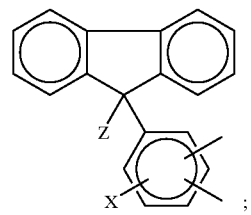

X represents a 2,3-epoxypropoxyl group; Y represents a hydrogen atom, a hydroxyl group or a 2,3-epoxypropoxyl group; Z represents a hydrogen atom, a phenyl group, a hydroxyphenyl group or a 2,3-epoxypropoxyphenyl group; and $R^1$ to $R^4$ are each independently selected from the group consisting of a hydrogen atom, an alkyl group and an aryl group having 1 to 10 carbon atoms and a halogen atom.

7. The compound according to claim 1, which further comprises, as a part of the $Ar^2$ groups contained in one molecule, a fourth atomic group represented by

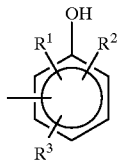

8. The compound according to claim 1, wherein the Ar¹ is a monovalent organic group represented by

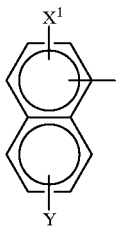

and the Ar² is a divalent organic group represented by

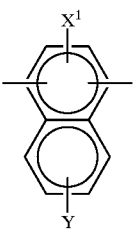

wherein $X^1$ represents a 2,3-epoxypropoxyl group; and Y represents a hydrogen atom, a hydroxyl group or a 2,3-epoxypropoxyl group.

9. The compound according to claim 1, wherein the Ar¹ is a monovalent organic group represented by

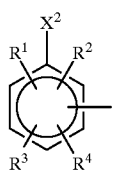

and the Ar² is a divalent organic group represented by

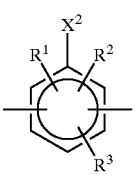

wherein $X^2$ represents a 2,3-epoxypropoxyl group; $R^1$ to $R^4$ are each independently selected from the group consisting of a hydrogen atom, an alkyl group and an aryl group having 1 to 10 carbon atoms and a halogen atom.

10. A compound which is a cooligomer represented by the following general formula (I):

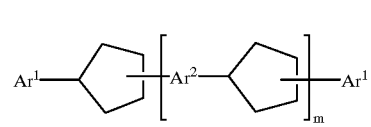
(I)

wherein m represents a positive number; Ar¹ represents at least one of monovalent organic groups selected from the group consisting of a fourth atomic group represented by

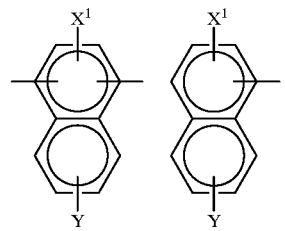

and a fifth atomic group represented by

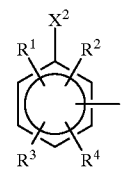

Ar² represents at least one of divalent organic groups selected from the group consisting of a first atomic group represented by

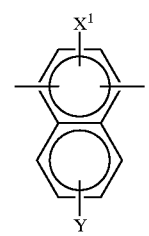

and a second atomic group represented by

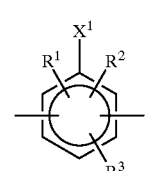

$X^1$ represents a 2,3-epoxypropoxyl group; Y represents a hydrogen atom, a hydroxyl group or a 2,3-epoxypropoxyl group; and $R^1$ to $R^4$ are each independently selected from the group consisting of a hydrogen atom, an alkyl group and an aryl group having 1 to 10 carbon atoms and a halogen atom;

and contains in one molecule at least one of the first atomic group and the fourth atomic group and at least one of the second atomic group and the fifth atomic group.

11. The compound according to claim 10, wherein the total number of said first atomic group and said fourth atomic group and the total number of said second atomic group and said fifth atomic group are in a ratio of from 20:1 to 1:20.

12. The compound according to claim 8, wherein the m is not more than 20 on the number average.

13. The compound according to claim 9, wherein the m is not more than 20 on the number average.

14. The compound according to claim 10, wherein the m is not more than 20 on the number average.

15. The compound according to claim 11, wherein the m is not more than 20 on the number average.

* * * * *